United States Patent
Ferenc

(10) Patent No.: US 10,823,861 B2
(45) Date of Patent: Nov. 3, 2020

(54) LARGE-AREA DETECTOR APPARATUS FOR PHOTOSENSOR, RADIATION DETECTOR, AND MEDICAL PET SCANNER APPLICATIONS

(71) Applicant: THE REGENTS OF THE UNIVERSITY OF CALIFORNIA, Oakland, CA (US)

(72) Inventor: Daniel Ferenc, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/350,943

(22) Filed: Nov. 14, 2016

(65) Prior Publication Data

US 2017/0123084 A1    May 4, 2017

Related U.S. Application Data

(63) Continuation of application No. PCT/US2015/031188, filed on May 15, 2015.
(Continued)

(51) Int. Cl.
  *G01T 1/29* (2006.01)
  *A61B 6/03* (2006.01)
  *G01T 1/20* (2006.01)

(52) U.S. Cl.
  CPC .......... *G01T 1/2985* (2013.01); *A61B 6/037* (2013.01); *G01T 1/2018* (2013.01)

(58) Field of Classification Search
  CPC .................................. G01T 1/2985
  See application file for complete search history.

(56) References Cited

U.S. PATENT DOCUMENTS 5,545,896 A  8/1996 Bratt et al.
6,201,257 B1  3/2001 Stettner et al.
(Continued)

FOREIGN PATENT DOCUMENTS

JP  2013-195295 A  9/2013
NO  2007-098493 A2  8/2007

OTHER PUBLICATIONS

Taconic TLC Brochure (Apr. 2005), 4 pages.*
(Continued)

*Primary Examiner* — David P Porta
*Assistant Examiner* — Shun Lee
(74) *Attorney, Agent, or Firm* — O'Banion & Ritchey LLP; John P. O'Banion

(57) ABSTRACT

A large area position-sensitive single-photon detector and radiation detector is described. Photon detectors are coupled to a large area panel configured with an equipotential feedthrough chamber that operates in combination with a photocathode of a hemispherical window to provide electrostatic focusing for the photoelectrons. The panels can be assembled into an enveloping structure, such as a PET scanner, which is globally and/or locally curved, such as into a sphere, ovoid, elongated cylinder, or similar structure providing significant sensitive surface surrounding an object, such as a patient being scanned in a medical positron emission tomography (PET) scanner. Increased sensitivity is provided in response to registering radiation by surrounding the patient, so that reduced patient radiation dosing levels are required.

24 Claims, 16 Drawing Sheets

Related U.S. Application Data

(60) Provisional application No. 61/993,906, filed on May 15, 2014.

(56) References Cited

U.S. PATENT DOCUMENTS

| | | | | |
|---|---|---|---|---|
| 7,205,546 B1* | 4/2007 | Kennedy | ............... | G01T 1/2985 250/363.02 |
| 2003/0034455 A1* | 2/2003 | Schreiner | .............. | G01T 1/1642 250/366 |
| 2007/0080295 A1 | 4/2007 | Hamill | | |
| 2013/0112856 A1 | 5/2013 | Ferenc | | |

OTHER PUBLICATIONS

Marketech International, Inc. Scintillator Crystals (Apr. 2006), 4 pages [retrieved on May 24, 2018]. Retrieved from the Internet: <URL: web.archive.org/web/20060408153444/http://www.mkt-intl.com:80/crystals/scintillator.html>.*

Ochi et al. Micro pixel chamber with resistive electrodes for spark reduction, Journal of Instrumentation, vol. 9 (Jan. 2014), C01039, 10 pages.*

Hernandes et al. The potential, electric field and surface charges for a resistive long straight strip carrying a steady current, American Journal of Physics vol. 71, No. 9, pp. 938-942 (Year: 2003).*

Korean Intellectual Property Office (KIPO), International Search Report and Written Opinion, dated Aug. 26, 2015, related PCT International Application No. PCT/US2015/031188, pp. 1-10, with claims searched, pp. 11-17. The relevance of non-English language reference JP 2013-195295 is indicated therein.

* cited by examiner

LARGE-AREA DETECTOR APPARATUS FOR PHOTOSENSOR, RADIATION DETECTOR, AND MEDICAL PET SCANNER APPLICATIONS

CROSS-REFERENCE TO RELATED APPLICATIONS

This application is a 35 U.S.C. § 111(a) continuation of PCT international application number PCT/US2015/031188 filed on May 15, 2015, incorporated herein by reference in its entirety, which claims priority to, and the benefit of, U.S. provisional patent application Ser. No. 61/993,906 filed May 15, 2014, incorporated herein by reference in its entirety. Priority is claimed to each of the foregoing applications.

The above-referenced PCT international application was published as PCT International Publication No. WO 2015/176000 on Nov. 19, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technological Field

This technical disclosure pertains generally to a positron emission tomography (PET) scanner, and more particularly to photosensitive panels and to a whole body PET.

2. Background Discussion

Medical diagnostics in many fields rely heavily on positron emission tomography (PET) scanners, such as the PET system seen in FIG. 1. This nuclear medicine functional imaging technique produces a three-dimensional image of various functional processes in the body. In using a conventional PET scanner, a patient is dosed with a radioactive drug, referred to as a "tracer", containing beta-plus or positron emitting nuclei. A scan is performed over a certain section of the patient's body, or in some cases sequentially, across the patient's body, to detect pairs of gamma rays emitted in annihilation of an emitted positron with an electron. The PET scanner detects the radiation given off by the tracer and produces three-dimensional maps of the body that provide clinically relevant information, such as distinguishing between normally and abnormally sugar-metabolizing tissues.

Traditional PET scanners are very complex, bulky and costly, primarily because of the 80-year old photomultiplier tube technology utilized. FIG. 2 depicts a ring-PET scanner without its cover. Aside from their complexity and cost, these sequential (ring) PET scanners have additional shortcomings.

In particular, the sensitivity of the scanner is limited, whereby the body being scanned must be dosed with significant amounts of the radioactive beta-plus tracer in order for salient physiological features to be discerned.

Accordingly, a need exists for a PET scanning apparatus and method which provide increased sensitivity thus allowing lowering patient radiation exposures. The present disclosure overcomes these shortcomings and others in providing gamma-ray detector panels, and an enhanced form of PET scanner.

BRIEF SUMMARY

Traditional PET scanners are configured in a ring format, and are used in a sequential scanning process, conventionally referred to as "whole-body PET", and sometimes referred to as a "drive-through PET", because the patient is slid through the opening in the PET ring as it is performing a sequential scanning operation, which is likened to cars coming up to a drive-through window. Operating these conventional systems requires the patient to be exposed to high radioactive doses.

In the present disclosure a new paradigm is disclosed which provides increased sensitivity and reduced cost and complexity for photo-radiation detection, and more particularly to a full body PET scanner capable of enclosing the human body and thus performing a whole-body PET scan in a single step.

FIG. 3 through FIG. 6 depict a number of the particular shortcomings of traditional sequential PET scanners. In FIG. 3 is shown an end view of a PET scanner, while FIG. 4 depicts a side view of the same scanner. Gamma-ray pairs (two of which are seen in these images) are detected in a ring pet which is subject to many lost gamma-ray pairs. In particular, many of the positron annihilation events occurring within the ring-PET proximity are lost to detection because one of the gamma rays escapes. In the majority of cases, both gamma rays from the same body segment will escape to the sides.

In FIG. 5 it is seen that the loss of Gamma-ray pairs not only leads to lowered signal levels, but also to the generation of noise. Accidental coincidences of gamma rays originating at all parts of a patient's body create high-level of background coincidence noise.

While a very small fraction of the body is examined by a ring-PET at any one time, the entire body is exposed to radiation, as exemplified in FIG. 6. A ring-PET may examine the entire body, but only in many independent sections. In all cases most of the harmful radiation dose is not providing signal information which will be used in the examination. On the contrary, most of this radiation emitted from the patient's body creates background noise that competes with the detection signal, thus requiring the high radiation doses in the tracer and increasing the duration of the examination procedure.

The present disclosure provides an apparatus and method for performing PET scanning on the whole body in a single scan. This not only speeds up the examination process, but interoperates with the scanning technology described to significantly increase scanning sensitivity and thus allow for reducing the doses of radiation given to the patient. This form of PET scanner is referred to in the disclosure as an ABALONE-PET scanner, which will be described in detail in the following sections.

In addition, large area photon detector panels are disclosed for detecting visible/UV light, for instance utilized in astro-particle physics, either to detect some light from space, or to detect light generated by radiation in different media (e.g., atmosphere, water, ice, or liquid scintillator, such as tanks filled with scintillating liquid).

Further aspects of the presented technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The disclosed technology will be more fully understood by reference to the following drawings which are for illustrative purposes only:

DETAILED DESCRIPTION

1. Introduction

Figure 1:
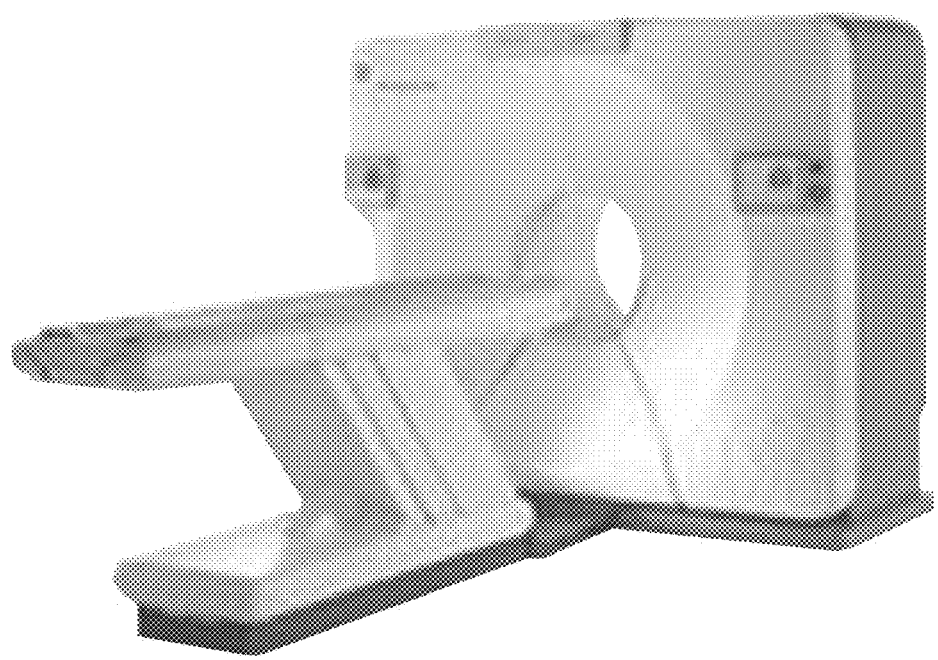
FIG. 1 is an image of a typical ring style PET scanner.
Figure 2:
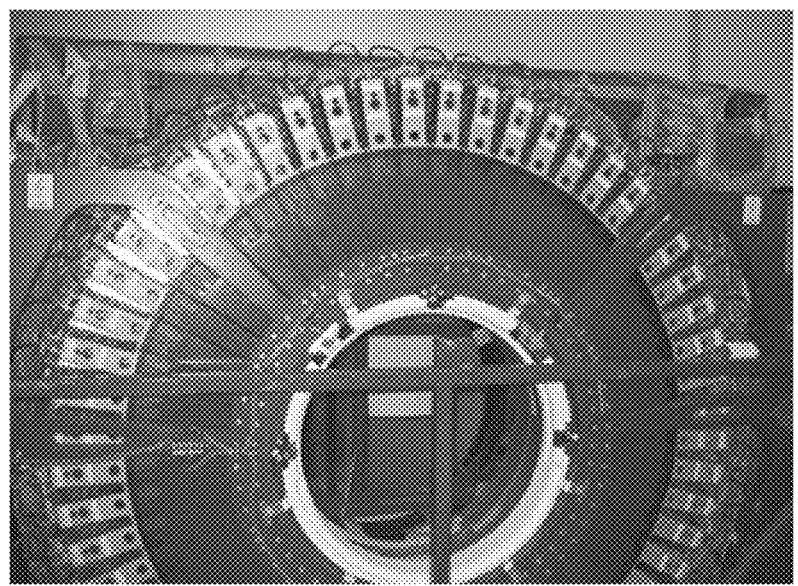
FIG. 2 is an image of the ring of a typical ring style PET scanner based on photomultiplier tubes.
Figure 3:
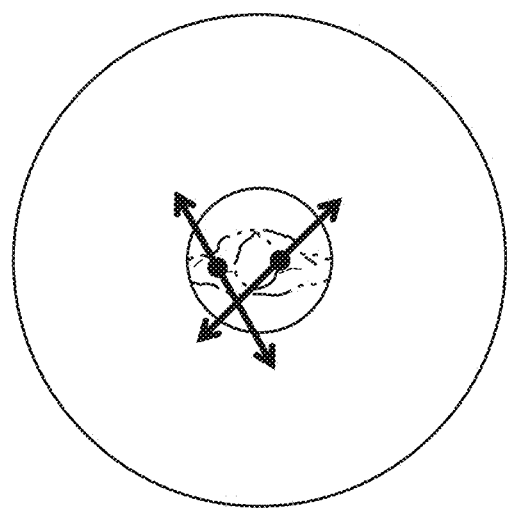
FIG. 3 through FIG. 6 depict schematics of Gamma-ray patterns in a typical ring style PET scanner.
Figure 4:
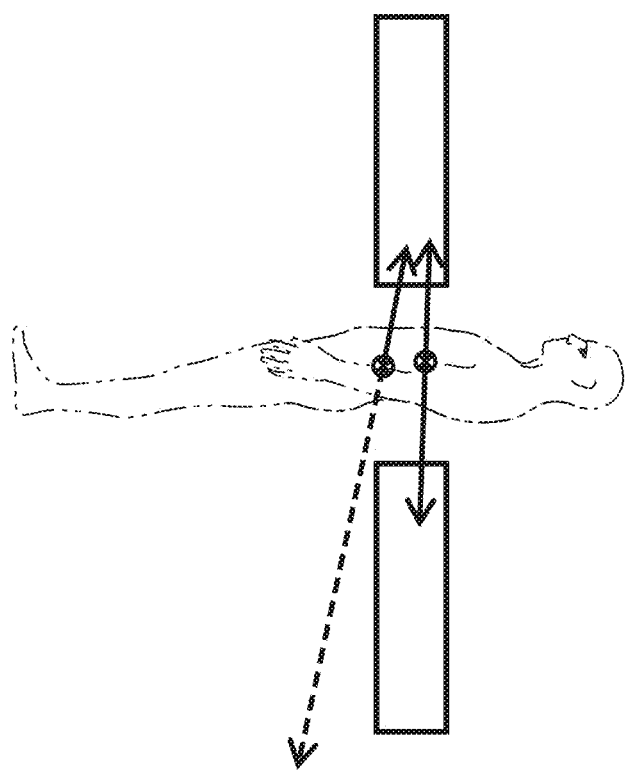
Figure 5:
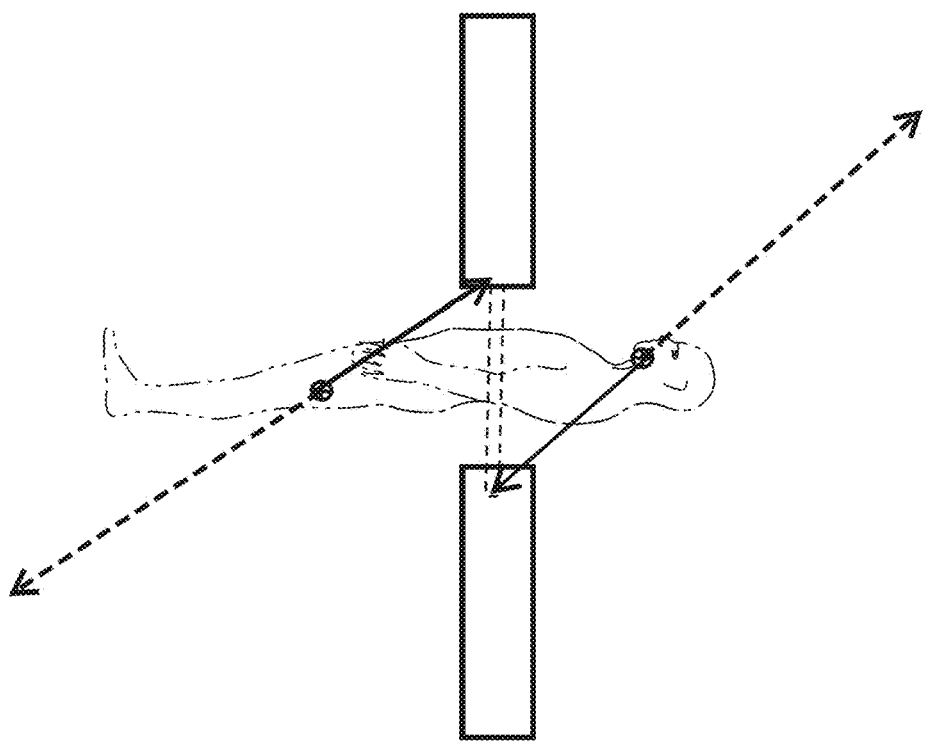
Figure 6:
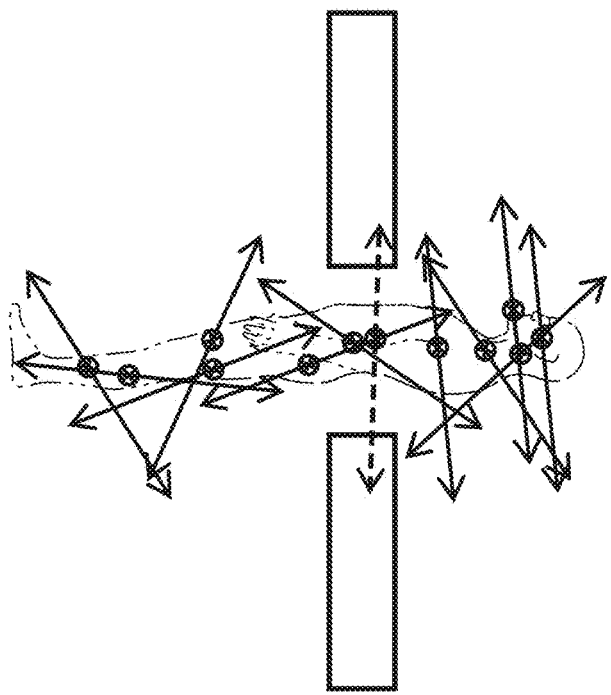

In the present disclosure a full body PET scanner, referred to herein as an ABALONE PET scanner, is described utilizing gamma-ray detector panels. In addition, the disclosure presents photon detector panels which are similarly constructed and allow for detection of other forms of light, such as visible and UV.

The disclosed full body PET scanner provide numerous structural benefits over prior PET systems. The ABALONE PET housing and structure is specifically configured for utilizing ABALONE photon detectors (disclosed in a previous application by the inventor, allowed US Patent Application Publication US 2013/0112856) which themselves provide numerous benefits over the use of PMTs. The ABALONE PET is configured with a large-area flat panel (or curved panel) photon detector structure, which is in contrast to a ring of wedge shaped sectors that start at the inner radius, first with scintillators and PMTs, then followed by 22-wire sockets, voltage dividers for PMT, preamplifiers, individualized power supplies, and cable bundles, extending the outer scanner radius by about 1 m. All those components are organized within a heavy support structure matrix as found in a conventional ring PET. In contrast, ABALONE PET provides a large-area low thickness (approximately 15 cm) and lightweight self-supporting gamma-ray detector shell, not incorporating any of the components of a conventional ring PET scanner, except of the scintillator layer.

2. ABALONE Photon Detector Panel Structure

The ABALONE photon detector units of the present disclosure are suited for the creation of large-area photon detector panels. An important component of the present disclosure is the multi-functionality of the ABALONE photon detector panels, which is only made possible by the ABALONE photon detector concept, about which it closely interoperates. These sandwich panels have a number of beneficial features: (a) configured for hosting the closely packed ABALONE photon detectors on its front face, forming a self-supported, compact multi-pixel camera; (b) provide an electrostatic configuration required by the electron optics, so that it properly functions within each ABALONE photon detector unit; (c) provides the rigidity and mechanical strength; (d) provides a universal distribution of the ground potential and the high-voltage potential for each ABALONE photon detector unit, throughout the panel, without any wires; (e) provides universal readout for each ABALONE photon detector unit, without cables; (f) hosts the G-APD sensors; and (g) provides sufficient mechanical stability to form, together with other identical photon detector panels, or gamma-ray detector panels, a large self-supporting structure similar to a geodesic dome.

In at least one embodiment, ABALONE photon detector panels or ABALONE gamma-ray detector panels are configured as rigid, undividable, permanently sealed blocks.

These panels can be submerged in water for a long period of time, dropped from a reasonable height, and exposed to vibration, sand, dust, moderate acids and bases, without compromising their electronic or structural integrity.

In at least one preferred embodiment, the ABALONE photon detector panels or ABALONE gamma-ray detector panels have virtually no internal cables, as all signals and supplied power are distributed within these shielded and environmentally sealed panels. The design of the ABALONE photon detector electronics allows for industrial-scale production without the need for separate, adjustable, power sources, such as those used with photomultiplier tubes (PMTs), and similarly without the requirement to perform laborious calibration and 'characterization' of individual PMT tubes.

The required thickness of an ABALONE photon detector panel element comprises only the camera components, plus, in case of ABALONE gamma-ray detectors the scintillator. Accordingly, the outer diameter of an ABALONE-PET dome may be kept small, in fact only about 15 cm larger than the inner diameter, in stark contrast to the use of PMTs in the prior art. The weight of an ABALONE-PET can be made significantly lower than that of a ring-PET. In view of the above, it is seen that the disclosed full body PET scanner provides a number of benefits over previous PET scanner devices.

3. ABALONE Technical Details

To understand positron emission tomography (PET), it should be recognized that a positron, which is the antiparticle of an electron, travels up to about 1 mm into tissue before annihilating with an electron. This annihilation results in generating two gamma rays which propagate in opposite directions, each having energy of approximately 511 keV.

It is important that both gamma rays emerging isotropically from a positron annihilation process must be detected by the PET scanner in coincidence. The objects of the present disclosure for an ideal PET scanner are as follows: (a) full angular acceptance, enclosing the entire patient's body; (b) 100% gamma ray detection efficiency; (c) perfect position resolution of gamma-ray detection points. Although of this list, only item (a) is practically realizable. A full solid angle maximizes the recorded number of radioactive decays in the body of the patient, minimizes the necessary radioactive exposure, and maximizes the benefit-to-harm ratio of the examination. Using the disclosed system, the radioactive dose to the patient may be reduced by a factor of approximately 80 (depending on implementation details), and 800 for whole body scans, compared to a typical ring-PET. The low level of radiation needed by the ABALONE PET should allow its relatively harmless use in pediatric applications. In addition, the system may be utilized in screening applications, such as screening of a healthy population (i.e., non-symptomatic patients) for the presence of cancer tissue in their bodies. Still further, the ABALONE PET scanner may be suitable for use in diagnostic studies of a number of conditions and bio-molecular processes that require very expensive bio-molecular tracers, and/or toxic tracers that may be given only in small quantities. In contrast to prior art, which is primarily centered around small-area ring-PET configuration, the ABALONE photosensor technology provides a useful platform for this full body scan object. Because all parts of a patient's body are examined in a single exposure (run), no stepwise motions are required, and the time required for a whole-body exam is possible in less than 10% of the time required utilizing prior art ring-PET systems.

By detecting gamma rays originating from the patient's entire body during the examination, ABALONE-PET maximizes the chances for the detection of the signal gamma-ray pairs, and minimizes the chances of recording fake coincidences of gamma rays originating from different parts of the patient's body. As a result of this enhanced detection, significant improvement in the signal-to-background ratio is provided.

The ABALONE photon detectors themselves consist of three vacuum-sealed elements, such as all being made of glass, which can be produced inexpensively using common glass-molding techniques. The only additional element, attached to ABALONE as part of the photon detector panel, is a small (e.g., factor 10,000 smaller than the photosensitive ABALONE photon detector area) Geiger-mode Avalanche Photodiode (G-APD).

The object of providing 100% detection efficiency may in principle be met with a very thick layer of NaI(TI) scintillator material (more than 50 cm), yet that would not be practical for many technical reasons, including parallax error, as well as cost factor. It has been found more practical to compromise with a rather thin scintillator, stopping 30-70% of gamma rays, but having an acceptable parallax error. Significant improvements are possible with special scintillation materials, commonly utilized in electron microscopes, based on rare earth materials and other heavy elements. These scintillating materials include, but are not limited to YAP, YAG, GSO, LYSO, LSO, LaBr:Ce, CeBr, etc., but they are, and will most likely remain prohibitively expensive for large-area applications. A traditional NaI(TI) scintillator of unusually high thickness (approximately 10 cm) presents a good working solution for the present disclosure.

Figure 7:
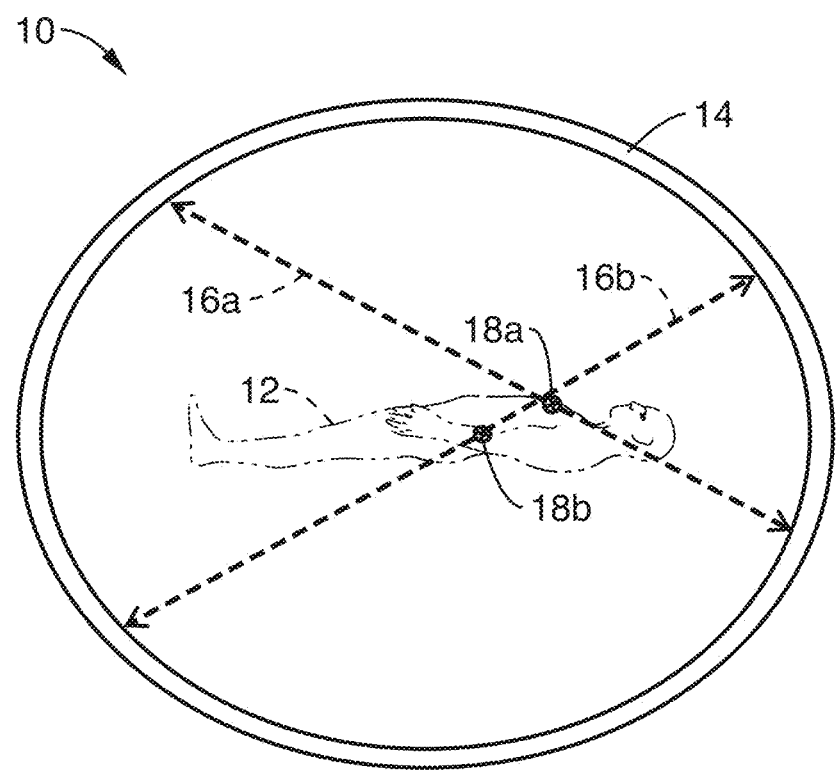
FIG. 7 is a schematic for a large diameter PET according to an embodiment of the present disclosure.
Figure 8:
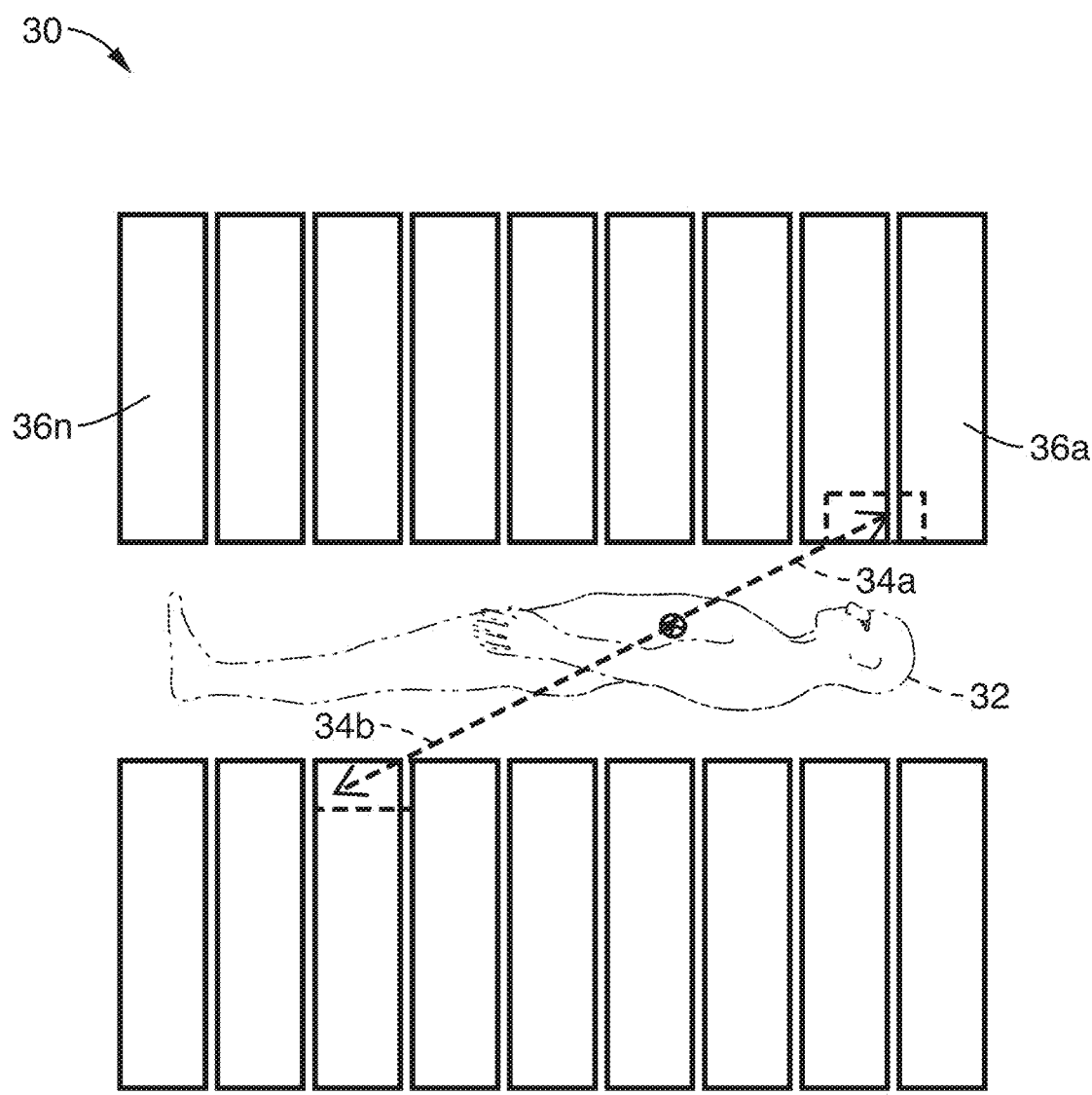
FIG. 8 is a schematic of detection problems which arise in extending a typical ring PET into a hypothetical tube-like PET scanner.

FIG. 7 and FIG. 8 depict a comparison of parallax error in a large-diameter PET scanner like ABALONE PET, compared with the hypothetical use of a plurality of ring detection sections. In the ABALONE embodiment 10 of FIG. 7, the gamma-ray detector envelope 14 curves not only around the longitudinal axis of the patient as in a ring-detector, but also curves around the transverse axis of the patient's body 12. Thus, both gamma rays 16a, 16b in the gamma ray pair originating in the patient at locations 18a, 18b are detected in the system with only minor parallax error due to the three dimensional curving within the ABALONE PET scanner.

A conventional ring-PET was already described in FIG. 3 through FIG. 6, in which only a small portion of the gamma rays are detected. In FIG. 8 we see a hypothetical PET configuration 30 built up from a number of ring PETs 36a through 36n. A patient 32 is seen with an example gamma ray pair 34a, 34b which extends out striking the different stacked PET rings. As can be seen from the ray intersection at the PET surfaces, this form of a long ring-type PET results in large incidence angles which introduce severe parallax error and would not be feasible for other reasons as well. In addition, such a small tube would further increase issues with claustrophobia, and problems arising when working with heavier patients.

It will be appreciated that parallax error in a large-diameter PET scanner, such as seen in FIG. 7, is by definition very low, so the scintillator thickness may be higher (e.g., by 50-100%) and more efficient in detecting gamma rays—which is in line with objectives previously outlined for this disclosure.

A method of precise gamma-ray hit position determination in large photosensors, was pioneered by H. Anger. By allowing the light from a small scintillator volume around the gamma conversion point to spread over several large PMTs, Anger provided the means to convert the light-intensity information, detected by the illuminated PMTs, into positional information that is much more precise than the size of each of the PMTs. The insertion of a transparent block (light distribution layer) between the scintillator and the PMTs allows the light to spread.

With the wide dynamic range, high resolution, single-photon sensitivity and high level of background suppression, it is possible to engage more ABALONE photon detectors in a single Anger logic group than prior art (e.g., 37, rather than 7). In embodiments such as FIG. 13 and FIG. 14, a thicker light distribution slab (layer) should be utilized to provide improved energy and position resolution.

An ideal PET system should also take into account ergonomic needs of the patients, such as providing adequate space for them to feel safe, including obese and disabled patients. A narrow (e.g., 75 cm wide) tunnel-PET of a 2 m length, such as hypothesized in FIG. 8, is therefore not a realistic option. An ergonomically acceptable PET according to the disclosure has an inner diameter of approximate range from 0.8 m to 3 m, and a length in the approximate range of from 2 to 4 m, such as seen in FIG. 7. The ABALONE-PET is designed around that requirement. Since the cost-per-area of ABALONE-PET will not be critical, in view of its configuration and low-cost material selection, so that a large-diameter ABALONE-PET using an Anger type logic light divider and traditional scintillators (both of larger thickness than conventional PETs) presents a realistic solution.

In addition, an ideal PET should be very robust, insensitive to water and dirt, portable and deployable to remote spaces in various kinds of transportation devices. ABALONE-PET should be suitable for that purpose, as the detector modules are thin, while each module may be completely sealed and made water-proof, and prepared for attachment to other modules, such as in utilizing side-by-side connections to form self-supported structures.

4. Gamma Ray Conversion—Photon Detector Panels

The disclosed ABALONE PET comprises a new paradigm in PET sensing, exemplified in the structure and photosensor panels of the ABALONE PET. These combination photosensor panels are constructed for interoperation with an ABALONE form of photon detector (or similar devices), the basic concepts of which were disclosed in a previous work of the inventor, as described in US Patent Application Publication US 2013/0112856 (application allowed awaiting patent issuance). The following provides a short summary on the construction of the ABALONE photon detector.

Figure 9A:
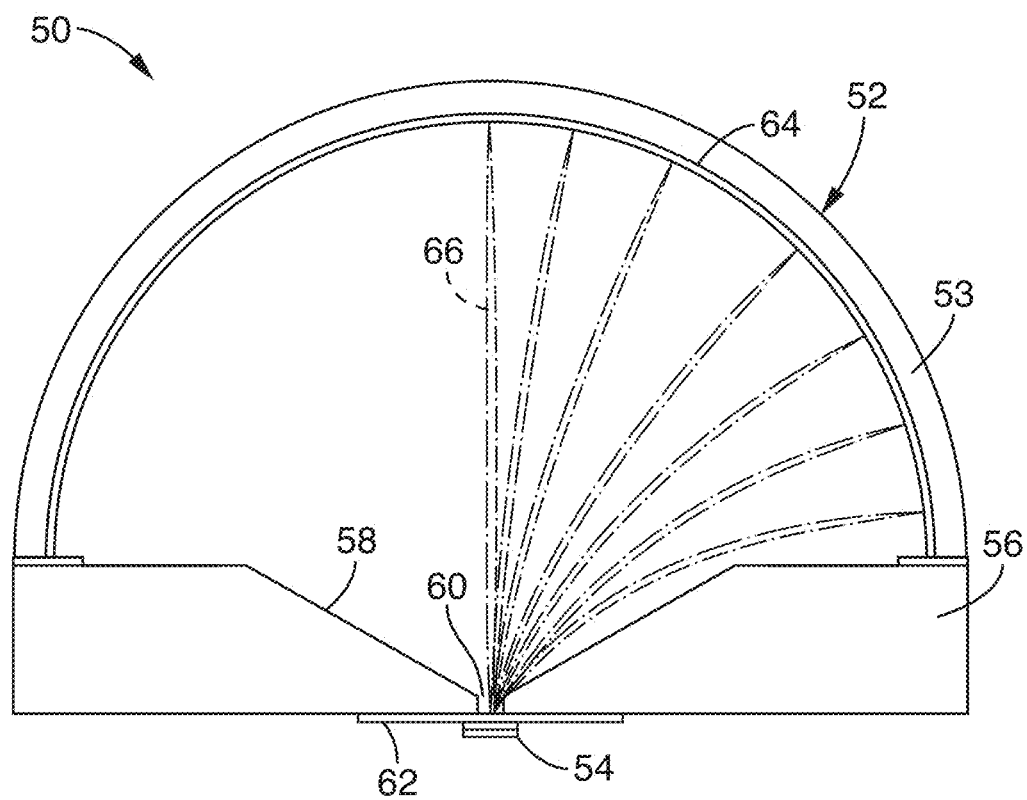
FIG. 9A through FIG. 9C are diagrams and images of a photosensor as utilized in an embodiment of the present disclosure.
Figure 9B:
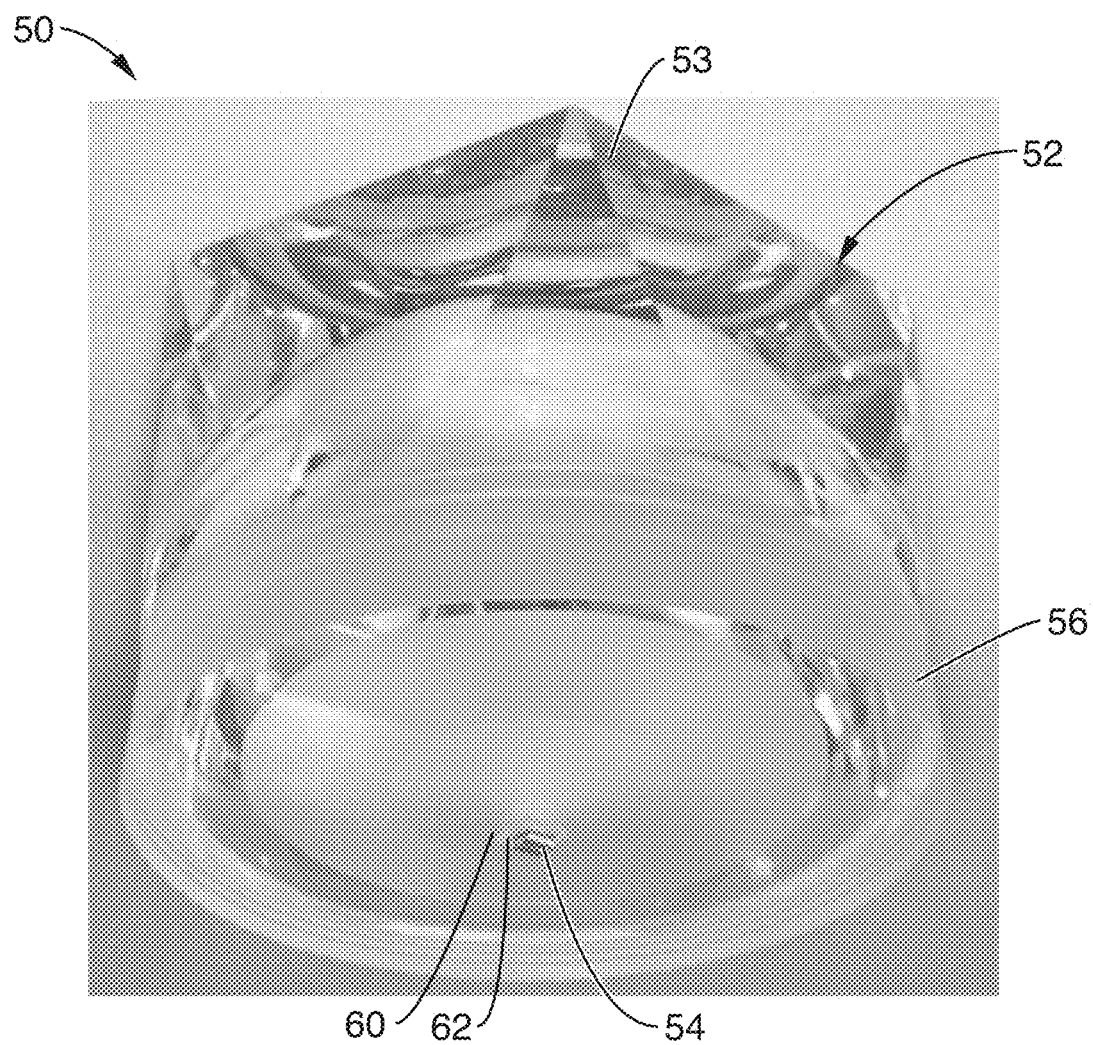
Figure 9C:
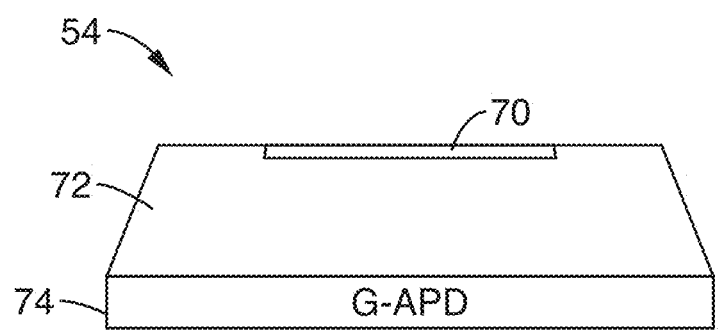

FIG. 9A through FIG. 9C depict an ABALONE photon detector, which is shown in an embodiment 50 for use with the ABALONE PET of the present disclosure. The cross section of FIG. 9A depicts the entire ABALONE photon detector 50, with a transparent upper housing 52 seen in FIG. 9B, and the electron detector 54 itself seen in FIG. 9C.

In FIG. 9A a photon detector embodiment 50 is exemplified with housing 52 seen with an outer sensor hemisphere 53 and photocathode 64, connected to a base plate 56, with ramped area 58 leading to an aperture 60 centered upon which is seen a seal 62, covered with the electron detector comprising a scintillator layer retained beneath the vacuum enclosure, and a photodetector 54 optically coupled to the underlying windowlet on the atmospheric side (e.g., a Geiger-Mode Avalanche Photodiode).

In FIG. 9B an embodiment of the photon detector housing 52 comprises a single molded dome piece of dielectric light-transmissive material (e.g., glass) having the exterior hemisphere 53, base 56, ramps (not visible) and aperture 60, upon which a photodetector 54 and seal 62 are seen mounted (with hemisphere evacuated). Referring back to FIG. 9A, the photon detector hemisphere 52 comprises an optically transparent material into which is disposed a thin film of semiconductor photocathode 64. Electron trajectories 66 are seen in dashed lines, from the photocathode to the scintillator-based electron detector device 54. This hemispherical window, along with its photocathode, and the electron detector are evacuated and hermetically sealed into a photon detector unit.

In FIG. 9C an example electron detector 54 is seen with a scintillator 70, windowlet 72, and a photon detector 74, depicted by way of example and not limitation as a Geiger-mode avalanche photo detector (G-APD). It should be appreciated that the term "scintillator" generally describes a material which emits light in response to being struck by a charged particle or a gamma ray, and is utilized here as an energy converter so that the photon detector 74 detects the energy of the electron by counting scintillation photons.

One of most unusual features of the ABALONE photon detector concept is the way in which it focuses electrons. The electric field within the vacuum enclosure that is required for proper electron focusing in the vast majority of usual vacuum devices (e.g., CRTs, ion guns and spectrometers) is created by electrodes mounted within the vacuum tubes, and connected via through-glass-feedthroughs to adjustable voltage sources outside the vacuum tube. The ABALONE photon detector has no through-glass-feedthroughs, neither any active focusing electrodes within the vacuum, as required in PMTs. The focusing action is rather provided by the distribution of conductors in the space outside the tube, behind the base plate. These conductors, either charged to the single operational high voltage of the ABALONE photon detector or to the ground potential, in conjunction with the photocathode surface and the conductive coatings on the base plate form the electron lens within the vacuum enclosure.

In the original ABALONE photon detectors this lensing was provided in each cell by including a rear electrically conductive dome. However, while the above electron optics solution was satisfactory for the operation of individual ABALONE photon detectors, it posed some problems for the integration of many ABALONE photon detectors into large-area panels hosting closely packed arrays of tubes, as in the ABALONE PET scanner, and photon detector panels disclosed herein. In particular, the extent of space required by these field-shaping back-hemispheres (essentially the same size as the ABALONE hemisphere itself) can be problematic, requiring larger housings, thickness and weight, while each cell must still be mounted within a structure. Second, the need to enclose each ABALONE photon detector with its back hemisphere, although radically less complex than having focusing electrodes within the vacuum enclosure and voltage regulators for them outside, nevertheless in some applications such as a PET would significantly complicate construction.

A novel solution was arrived at for the present disclosure toward solving this problem. A creative breakthrough verified by extensive numerical simulations led to the development of a sensor structure which, instead of closing the equipotential surfaces behind each ABALONE photon detector in an array, these equipotential surfaces could be broken and transmitted from tube to tube in an array. This creative development, as backed by numerical simulations obtained by using both the Simion and the Lorentz 3-D software packages, led to a special sub-class of solutions allowing for the equipotential lines to be squeezed between two narrowly spaced plates. It should be noted that the present disclosure can utilize any of the front dome and detector embodiments described in our previous work, or devices of a similar nature, which are configured as described herein. The front dome and photon detector are preferably evacuated to an ultrahigh vacuum level of about $10^{-7}$ Torr or better. In at least one embodiment, the dome is formed with an sealed base plate (56 in FIG. 9B) having an electron detector and seal.

Figure 10:
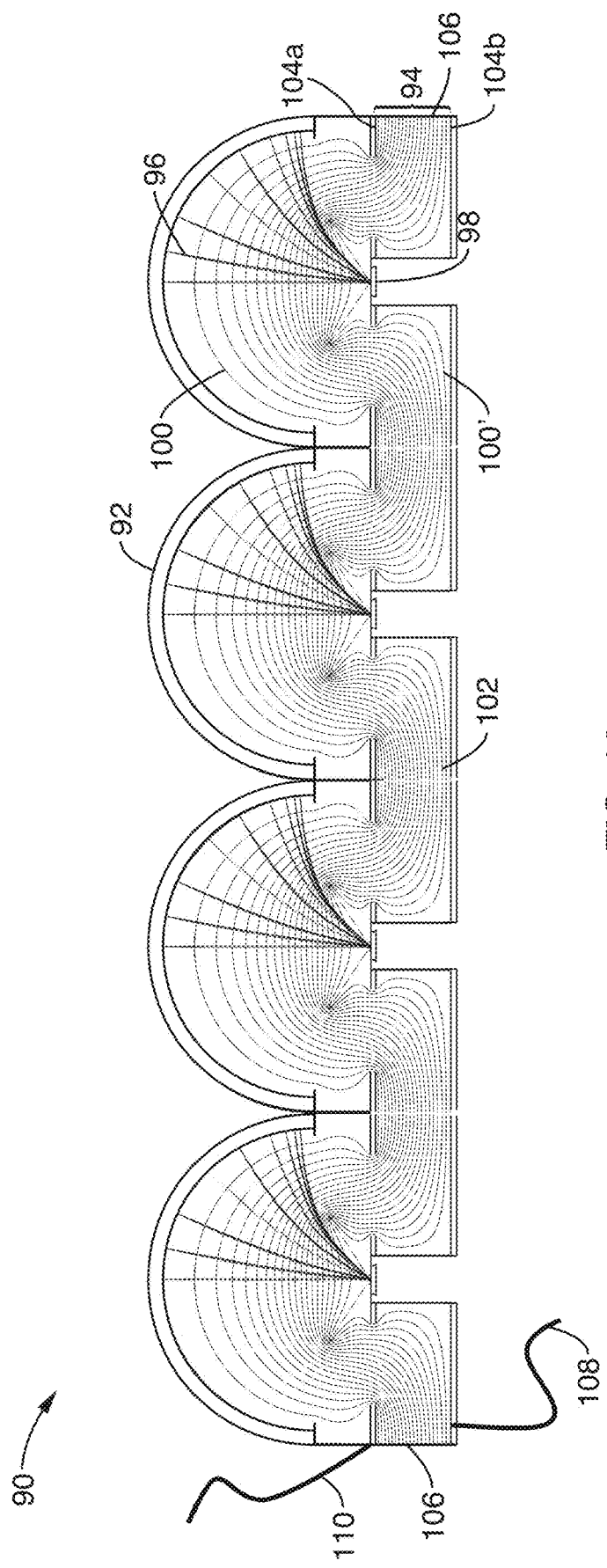
FIG. 10 is a cross-section of electrical field lensing within an ABALONE photon detector panel according to an embodiment of the present disclosure.

FIG. 10 illustrates an example embodiment 90 with dome structures 92 coupled to an ABALONE photon detector panel 94 (bounded by an upper and lower plate) configured to retain an equipotential feedthrough channel beneath the sensor domes. In the figure, electron trajectories 96 are seen directed at the combination scintillator-photo-detector 98 in response to a proper distribution of electrical potentials. In particular, electrical equipotential lines 100 are seen in the upper dome structure which are carried as equipotential lines 100' through an equipotential feedthrough chamber 102 defined between a first panel exterior 104a, and a second panel exterior 104b, and bounded by termination strips 106. Obviously, in the three dimensions of a photosensor panel structure the equipotential lines are actually equipotential surfaces. The second panel (bottom) is coupled to a ground potential 108, while the upper panel is coupled to a high voltage source 110 which also connects into the conductor on the interior of dome 92. The ABALONE photon detectors may properly focus photoelectrons to the electron detector for high voltages higher than 1 kV, but the signal created in a LYSO scintillator by each electron is high enough for useful detection in a PET scanner application only for high voltages above 5 kV. Optimal results with LYSO scintillator have been achieved with high voltages of 20-30 kV. It should be appreciated, however, that other scintillator materials may require different levels of this high voltage for optimal operation.

Figure 11:
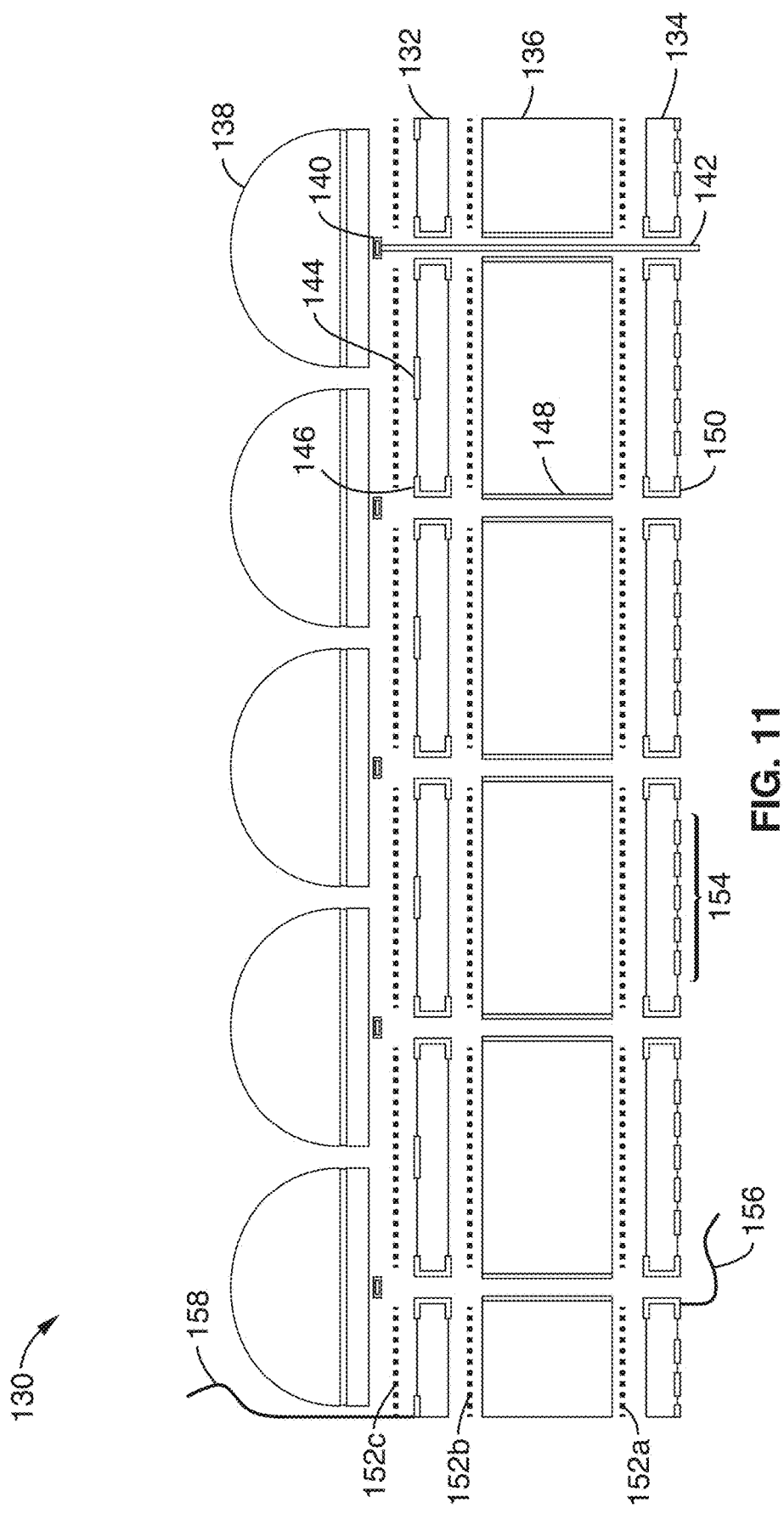
FIG. 11 is a cross-section of a structure for an ABALONE photon detector panel according to an embodiment of the present disclosure, shown using PCB1 an PCB2 as top and bottom plates.

FIG. 11 illustrates an example embodiment 130, showing with greater particularity the designed interoperation between ABALONE photon detectors and the structure for retaining them in an ABALONE photon detector panel. In the figure, printed circuit boards (PCBs) preferably comprise the upper plate 132, and lower plate 134, spaced for the equipotential feedthrough channel 136. For proper operation, the spacing between the upper plate 132 and bottom plate 134 should be approximately one-fourth of the inner dome diameter. For example using an ABALONE photon detector having a 50 mm inner dome, requires a spacing between the upper and lower plates of 12.5 mm, with a plate thickness of approximately 1 mm.

Top plate 132, preferably comprises a conductive pattern on the top layer of PCB1 facing the backs of the ABALONE photon detectors, which makes an electrical contact with the outer electrode of each ABALONE photon detector unit, such as at a dome perimeter conductive ring. At the center of each perimeter conductive ring (centered below each ABALONE photon detector unit) is a hole in PCB1 surrounded by a conductive ring. In the lower plate 134 PCB2 a similar conductive ring is found around a hole centered in alignment below the conductive ring in PCB1 for attachment of a conductive bridge (cylindrical) between the two layers.

It will be noted that the plate spacing (between 132 and 134) is small, (about one-fourth of the inner diameter of the sensor dome) compared to the size of the back-hemispheres utilized in the previous standalone ABALONE photon detector devices, whose size was equivalent to the exterior size of the front dome. A plurality of ABALONE photon detectors 138 with attached electron detector 140 having leads 142 are shown for attachment to the upper plate 132.

The upper plate (PCB1) 132 has a surface configured with two conductive material patterns, a first set of conductors 144 for distributing the universal high voltage, to the conductive layer of each of the ABALONE photon detector bases and domes, and a second set of conductors 146 as ground potential feedthrough (via) rings. These via rings are not electrically connected on the upper PCB1 132, but are configured for conveying ground potential from ground potential conductive rings 150 on PCB2 134, through the conductive surface of ground-potential tubes 148 up to ring 146 in this upper plate. In one embodiment, the diameter of the conductive ground-potential tubes 148 should be about 7.8 mm for ABALONE photon detectors with a hemispherical dome of 50 mm inner (photocathode surface) diameter. The lower plate 134 (PCB2) is conductive over its entire surface (or a closely spaced mesh pattern) facing the upper plate 132 (PCB1) board, and retaining a ground potential. A ground potential connection 156 and high voltage potential connection 158 are shown extending from the composite ABALONE photon detector panel for external connection of these power sources. The side of lower plate 134 (PCB2) which is opposite of the upper plate 132 (PCB1) can be patterned 154 with traces, or circuitry, or connectors, or device sockets, or other structural or electrical items, or a combination thereof as desired. It is contemplated that traces 154 would at least provide for routing conductive traces for connecting individual sensor readouts. The printed circuit material of the upper and lower plates may comprise materials, such as fiberglass (e.g., a thick G-10 board), glass, fused silica, quartz, Teflon (Polytetrafluoroethylene), Teflon composites (Polytetrafluoroethylene composites), and composite structures in general, or any other suitable material.

An equipotential feedthrough channel 136 is retained between plates 132, 134 (PCB1 and PCB2). As previously described, this spacing between top and the bottom plates is preferably about one-quarter of the ABALONE photon detector diameter. In at least one embodiment, a special lightweight electrically insulating material is preferred for filing region 136 between plates 132, 134, such as Rohacell foam, or Airex material, or any material of similar electrically insulating properties.

In the example of FIG. 11 a structural panel is shown being constructed as a sandwich of this light insulating core material between the two printed circuit boards (PCBs) adapted for conveying the signals to the ABALONE photosensor units. In this example, a thin epoxy material 152a, 152b, is shown distributed between the foam core 136 and exterior plates 132, 134, to create a rigid panel structure. The two PCB boards are thus permanently adhered to the core, forming a thin composite board having significant structural strength. ABALONE photon detectors 138 are then mechanically coupled to this rigid panel, such as by utilizing epoxy 152c at the interface between these two structures. It will be appreciated that each ABALONE photon detector panel may be fabricated into various closed shapes (e.g., rectangles, triangles, hexagons, and so forth) or any other suitable shapes or combinations of shapes. These panel modules can be configured for attachment to one another by their sides by detachable mechanisms, forming larger planar surfaces useful as gamma cameras for medical imaging using techniques including those of SPECT and PET scanners.

Figure 12:
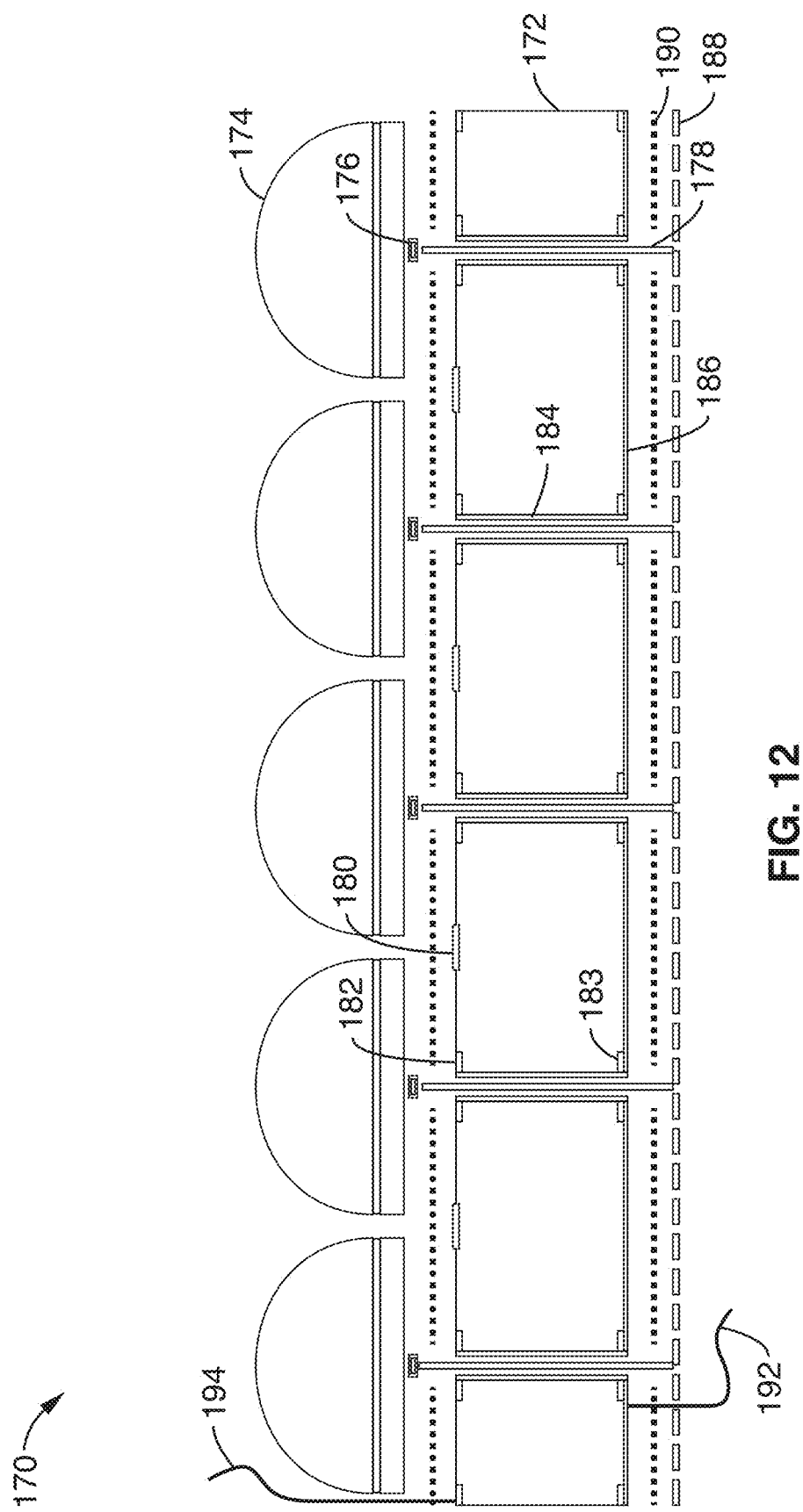
FIG. 12 is a cross-section of a structure for an ABALONE photon detector panel according to an embodiment of the present disclosure, shown using other materials aside from PCB1 and PCB2 as top and bottom plates.

FIG. 12 illustrates an example embodiment 170 of a rigid panel structure which differs from that of FIG. 11, in that one or both of the PCBs are eliminated and replaced with directly placed conductive layers/traces. A plurality of ABALONE photon detectors 174 with attached electron detector 176 having leads 178 are shown for attachment to the panel structure 172. An electrically insulating material (e.g., insulating foam) 172 is retained as the equipotential feedthrough channel upon which the gamma conversion photodetector units 174 are to be electrically and mechanically connected. It should be appreciated that the insulating material layer 172 may include insulating structures within it, and/or upon it, as desired (e.g., higher density material used as an exterior layer, or an internal skeleton of high density material to be filed with a lower density insulation or air) to increase structural rigidity at a lower weight penalty than simply using a higher density homogenous core material. In this example, pads are still disposed on the core for high voltage connection 180 to the photosensor units 174, and for ground potential rings 182 at the interface with the units 174, configured for connection through ground conductive tubes 184 to a lower ring 183 coupled to ground potential surface 186. Alternatively, tube 184 may connect directly to ground potential surface 186.

The conductive rings 182, 183 and tubes 184 may be fabricated in any desired manner, for instance as conductive pedestals having an outer flange (ring) coupled to a hollow shaft. The hollow shafts of opposing pedestals are configured for insertion on opposing sides of the core and engagement of one another mechanically and electrically. One of ordinary skill in that art will appreciate that numerous alternative mechanisms could be described for providing these conductive rings and pathways without departing from the present disclosure. This lower ground potential surface 186 may comprise a solid conductive material layer (e.g., aluminum, copper), or a clad material (e.g., copper clad plastic or PCB material), or other material or material combinations configured for distributing this ground potential. It should be recognized that although electrical connectivity to and from the separate ABALONE photon detectors are described as provided through traces in a PCB or through additional layers, these signals can be conveyed in other ways, including carrying these signals through wiring harnesses, or similar non-planar structures. A low voltage and readout network 188 is seen separated from the ground potential plane 186, by an insulator 190 layer, such as an electrically insulating film. The low voltage and readout network could comprise a PCB, a route and place board, bus bars, or other structures for electrical distribution as desired. Again a ground potential connection 192 and high voltage potential connection 194 are shown extending from the composite panel for external connection of these power sources to be distributed across the panel.

This rigid panel structure provides several functions: (a) replacing the back-hemisphere from the separate sensors in the original ABALONE photon detector application, while providing a workable reshaping of the equipotential surfaces that provide precise point like electron focusing within all the ABALONE photon detectors mounted on the front surface of the ABALONE photon detector panel; (b) distributing the electric field from photon detector to photon detector across the entire photon detector panel, until it terminates in a terminator at ends of a panel; (c) shielding of the high voltage; (d) providing of structural rigidity to provide mechanical stability of the rigid composite panel (it may be designed specifically for the expected load); (e) serving as the only high-voltage distributor for the entire ABALONE photon detector array; (f) and collecting all the readout lines from each ABALONE photon detector leading them to a single connector through a network of printed circuit traces. It should be appreciated, however, that although the ground potential, high voltage potential, and signal lines are preferably routed solely through this combination of PCBs in the composite structure, a designer could alternatively choose to add other layers and/or wiring, or even fiber optics (with appropriate electrical to optical converters), for carrying these and other signals without departing from the teachings of the present disclosure.

It should be appreciated that the present disclosure can also be implemented as (a) large area photon detector panels, and/or (b) large area gamma-ray detector panels. The large area photon detector panels are configured for detecting visible/UV light (not gamma rays or any kind of radiation). By way of example and not limitation, these are particularly well-suited for use in astro-particle physics, either to detect some light from space, or to detect light generated by radiation in different media, for instance the atmosphere, water, ice, or liquid scintillator (huge tanks filled with scintillating liquid). In the latter cases the radiation can be, for instance a cosmic gamma ray that interacts with the atmosphere and creates showers of secondary particles at high altitude (approximately 10 km), and each of those electrically charged particles emits VISIBLE/UV Cherenkov light or fluorescence light in the atmosphere. In another instance, the light being detected may be a neutrino that creates charged particles in ice or water (or liquid scintillator), which then create Cherenkov, fluorescence or scintillation light in these media. In the case of the large-area gamma-ray detector panels, the ABALONE photon detector panels incorporate a scintillator layer in the same package, and this layer converts gamma rays into visible photons, just like in the previous case in which one of those external media (e.g., atmosphere, water, ice) provided the conversion. These gamma-ray detector panels may be used in the construction of PET scanners and nuclear security detectors, while the large area photon detector panels may not, because they do not have a scintillator.

It should be appreciated that in typical embodiments of the present disclosure there are two scintillators. The first is an outer scintillator that covers photosensors over the entire panel, and it is thick (e.g., approximately 10 cm), and preferably comprises NaI(Tl). That scintillator is exposed to gamma rays, either from a positron annihilation or a nuclear material. In response to the gamma-ray impact that first scintillator creates visible light; for example 19,000 visible light photons for each fully absorbed 511 keV gamma ray from a positron annihilation. The majority of these photons travel through the light distribution layer between the scintillator and the closely packed ABALONE photon detector array and spread over many ABALONE photon detectors, where they are converted with certain quantum efficiency (e.g., typically about 20%) into photoelectrons. Each of these electrons in each ABALONE photon detector is then focused and accelerated towards a second scintillator, which is the first of the two components of the electron detector. That second scintillator should be at least 2 micrometers thick to stop all the electrons of up to 30 keV energy, while less than about 1.5 mm thick for mechanical reasons. It can be made from a variety of materials used for electron microscopy, X-ray detection and gamma-ray detection, including LYSO, which have been used in prototypes according to the disclosure. Each electron of an energy of 20 keV creates about 500 photons of visible light in LYSO. The light created within that second scintillator is transmitted through the windowlet to its outside (non-vacuum) surface, and detected by a suitable photosensor. A preferred type of photosensor for detection of that light within the prototype studies is that of a Geiger-Mode Avalanche Photodiode (G-APD). The G-APD is brought in optical contact with the windowlet, such as using an optical cement or an optical jelly. After all losses due to photon absorption and detection efficiency, a typical G-APD will detect about 50 photons out of the 500 created by the impact of an 20 keV electron in the LYSO crystal. Each initial photoelectron emerging from the ABALONE photocathode upon a photon impact therefore leads to the detection of the signal of 50 photons in the G-APD, which results in a very high signal level over electronic noise, which is on the level of one photon.

5. Radiation Detector Panels

The panels described above, which are preferably utilized as prefabricated units as building blocks for large-area structures of various forms, such as flat or globally curved sensing arrays. The globally curved surfaces may be of open geometry (like e.g., hemispheres), or closed (like e.g., spheres or ellipsoids). The preferred shapes of these elementary building block panels are hexagons and pentagons, but they may also be rectangles, or any other desired shape.

The ABALONE photon detector panels may be used directly for light detection (e.g., after some focusing device, such as a lens, Fresnel lens, mirror), or for radiation detection (such as gamma rays), in conjunction with other materials (such as scintillators [e.g., liquid, crystal, plastic], Cherenkov radiators [e.g., water, ice, atmosphere, gases, various liquids]). In the case of solid scintillators, the ABALONE photon detector panel forms a single composite panel together with the scintillator layer and typically an intermediate light-distribution layer (Anger camera principle). That particular device, ABALONE radiation detector, is discussed below as a separate embodiment and it allows the design and construction of a large-area PET scanner, the ABALONE-PET.

The ABALONE radiation detector panels are self-contained and in at least one embodiment are permanently sealed panels, made ready for attachment to each other, to form large structures, (hexagonal panels form large flat radiation detectors, while a combination of hexagons and pentagons may form spheres and more complex shapes). In at least one embodiment, these panels have no loose or removable parts, they are electrically insulated on all sides, and environmentally sealed by an epoxy or hardened silicon rubber coating, and in one embodiment would have no serviceable parts, and in case of failure would be replaced.

Figure 13:
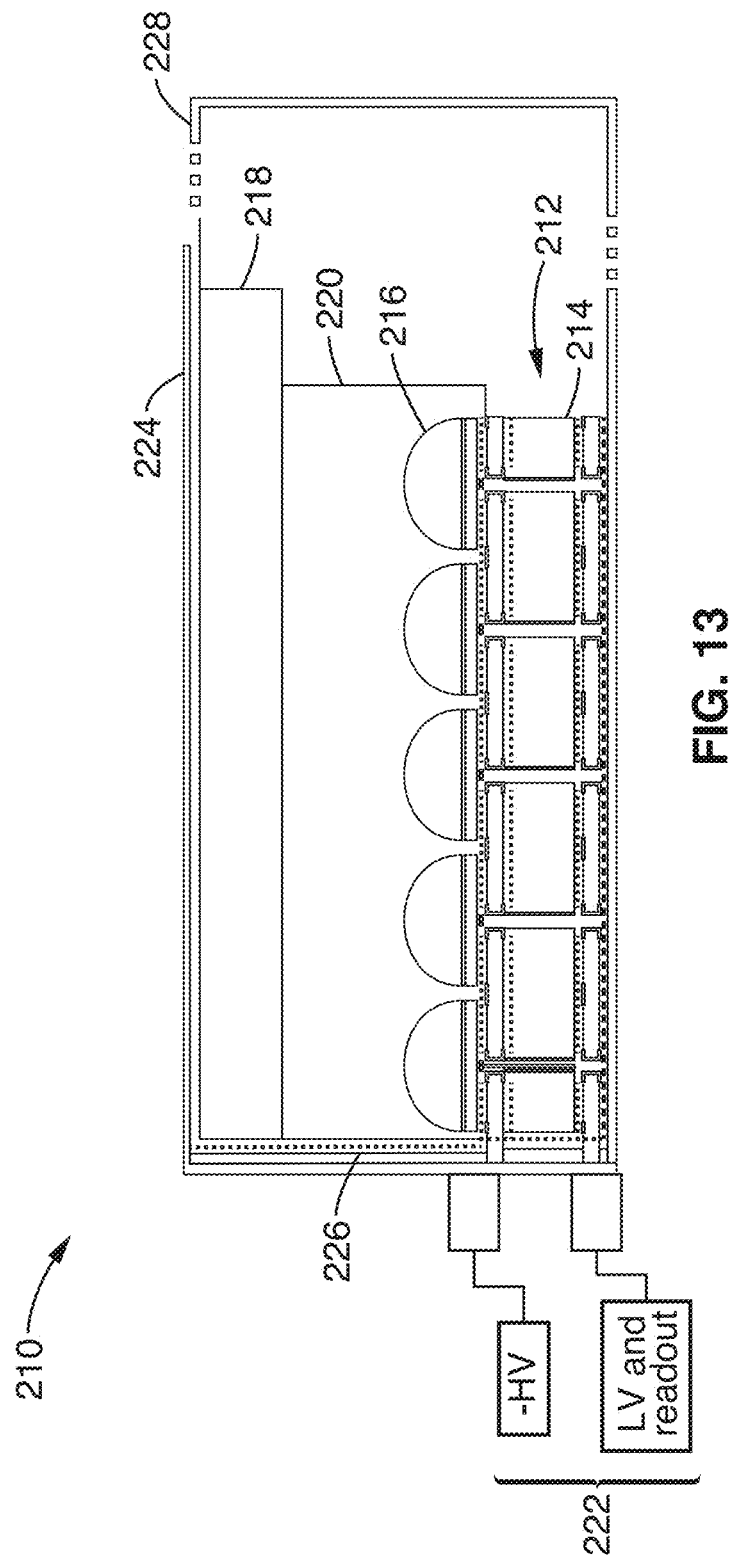
FIG. 13 is a cross-section of a structure for an ABALONE gamma-ray detector panel in a housing according to an embodiment of the present disclosure, shown with an additional light distribution and scintillator layers.

FIG. 13 illustrates an example embodiment 210 of a radiation detector panel 210 utilizing a photosensor board 212, having the structure 214 of upper and lower plates supporting an equipotential feedthrough channel and upon which ABALONE photon detectors 216 are coupled, these elements being described in previous embodiments. The panel 210 is seen having a scintillator layer 218 over a light distribution layer 220 above the detectors 216. The scintillator and light distribution layers may comprise any monolithic, or subdivided material which is a solid, liquid, or gel having the desired light scintillation and/or distribution properties. The scintillator may comprise any desired structure or material, such as selected from the group of materials consisting essentially of PEN, NaI, NaI:TI, CsI, GSO, LYSO, LSO, LaBr:Ce:CeBr, and other solid, crystal, liquid, gel, gas, or plastic scintillators. The thickness of the light distribution layer is preferably in a range of from one ABALONE photon detector radius to about eight radii, although other thicknesses from zero on up may be utilized. In at least one embodiment, the transparent light distribution layer and scintillator layer, join all units into a monolithic assembly. Radiation detector 210 is seen encapsulated having a reflective surface 224, a rigid exterior surface 228 (e.g., fiberglass) and epoxy resin 226, such as for joining adjacent panels. The external layer of optically and electrically insulating material may comprise prefabricated fiberglass material, or black epoxy resin with glass-fiber reinforcement, or epoxy resin with glass-bead filling, or other suitable optically opaque material offering sufficient strength and impenetrability for the atmosphere, covering the entire composite package on all sides, making it water tight, shock-proof, light tight and high-voltage safe. Connectors 222 are seen in the figure extending from the sealed panel for connecting power and readout signals. It will be appreciated that any desired number or configuration of electrical signal connections may be utilized without departing from the present disclosure. In additional, structures can extend or be recessed (not shown) in the panel for allowing for secure mechanical interconnection of the panels.

Figure 14:
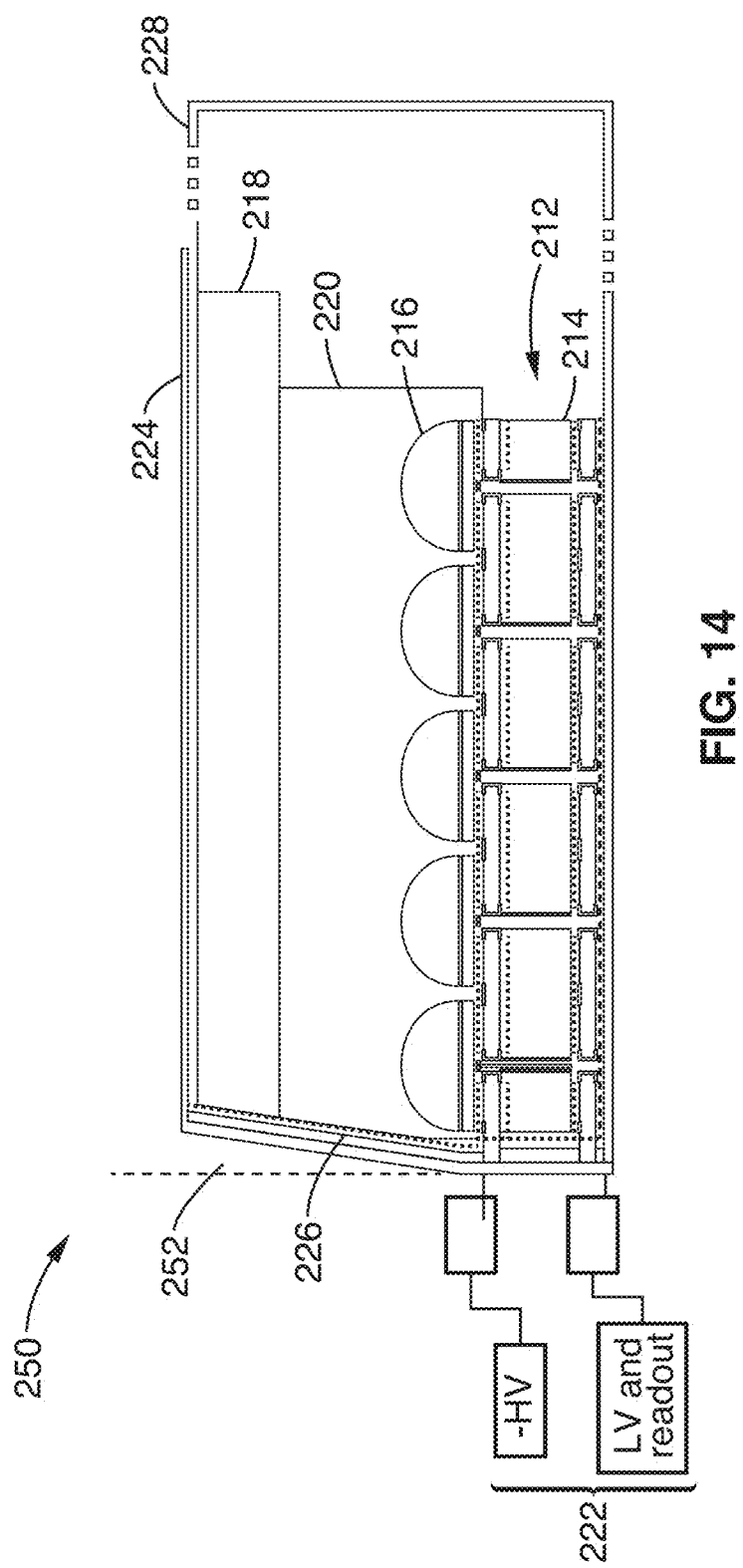
FIG. 14 is a cross-section of a structure for an ABALONE gamma-ray detector panel of FIG. 13, shown in a tapered housing according to an embodiment of the present disclosure.

FIG. 14 illustrates an example embodiment 250 of a tapered ABALONE radiation detector panel. This panel is substantially identical with that of FIG. 13, however, it is configured with one or more tapered end sections 252 that allow simple interconnection with other panels into a curving structure, instead of a flat structure.

Figure 15:
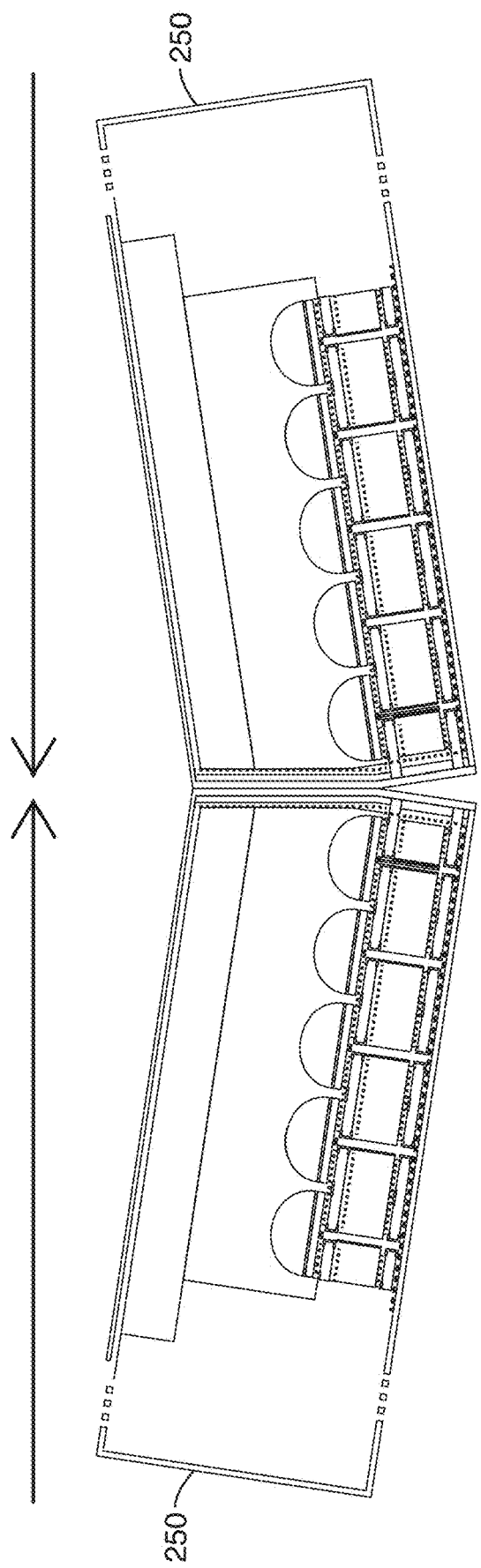
FIG. 15 is a cross-section showing joining of ABALONE gamma-ray detector panels as seen in FIG. 14 according to an embodiment of the present disclosure.

FIG. 15 illustrates an example of joining two of the tapered ABALONE radiation detector panels 250.

Figure 16:
FIG. 16 is an image of materials utilized in an ABALONE photon detector panel according to an embodiment of the present disclosure.

FIG. 16 depicts some panel materials, including ABALONE glass domes provisionally mounted on top of the base plates 270, printed circuit material 272 as an upper plate for receiving ABALONE photon detectors, insulating material 274 for retention between upper and lower plates, and a conductive layer 276 for the lower plate, shown prior to assembling into the sandwich sensor panel, such as by utilizing an adhesive or more preferably an epoxy resin.

Figure 17:
FIG. 17 is an image of multiple ABALONE photon detector panels joined into a faceted curving section of panels according to an embodiment of the present disclosure.

FIG. 17 illustrates an example embodiment showing five radiation detector panels joined into a curving structure, with a conductive surface (e.g., shown as unprocessed PCB) at the center. For the sake of demonstration, only one of the panels is shown with simulated domes of the ABALONE photon detector in place. In this example embodiment, the section spans 140 cm, by way of example and not limitation. It will be appreciated that the tapered ABALONE radiation detector panels can be coupled into a spherical shape, with flattened hexagonal panels on its exterior, such as appearing somewhat like a soccer ball.

Figure 18:
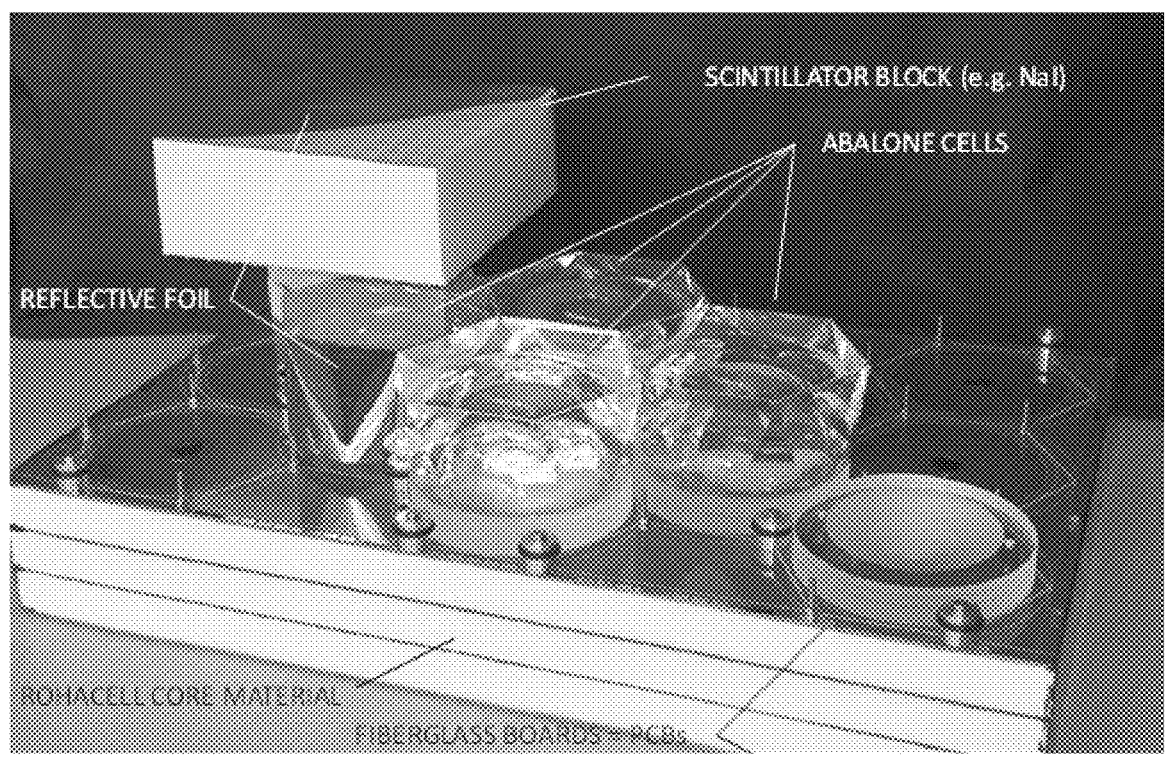
FIG. 18 is an image of a composite structure of a gamma-ray detector panel according to an embodiment of the present disclosure, showing core material, ABALONE photon detectors, light distribution blocks, a scintillator layer, and reflective foils.

FIG. 18 illustrates an example embodiment of sections from a radiation detector panel, showing the sandwich core materials, the upper printed circuit board upon which the ABALONE photon detector cells are mounted having hemispherical domes which are extended to provide light distribution from a plane (where it meets the scintillator material). A reflective material (e.g., reflective foil) is seen around one of the ABALONE photon detectors, while a scintillator block (e.g., NaI) with a reflective material top are seen over the light distribution domes.

It should be appreciated that the photon and the radiation detector panels are not limited to being fabricated with a sandwich structure, as they may be made in structural configurations, such as from a monolithic block of glass. Elements in the structure may be machined or molded. In one embodiment the panel is fabricated from a block of quartz, either monolithic or having an internal structure, for applications requiring minimum radioactivity from the sensors (quartz is ultrapure). A quartz board would then have a pattern of very thin electrical layers on its top and its bottom. One of ordinary skill in the art will appreciate that a large number of alternative configurations can be advanced without departing from the teachings of the present disclosure. It should also be appreciated that the disclosed flat panel construction embodiments and techniques can be generally applied to create smoothly curving panels, by utilized curved substrates and materials (PCBs with insulating cores).

6. Large-Area Radiation Detector Including Medical Pet Scanner

Figure 19:
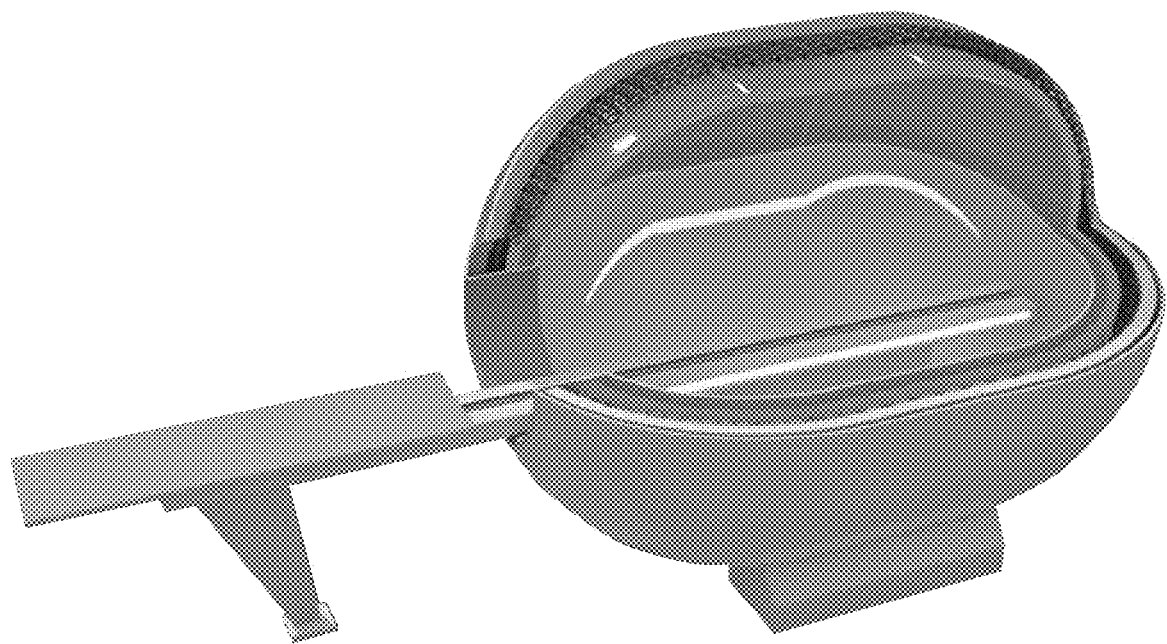
FIG. 19 and FIG. 20 are images depicting different external shapes of an ABALONE PET scanner according to an embodiment of the present disclosure.
Figure 20:
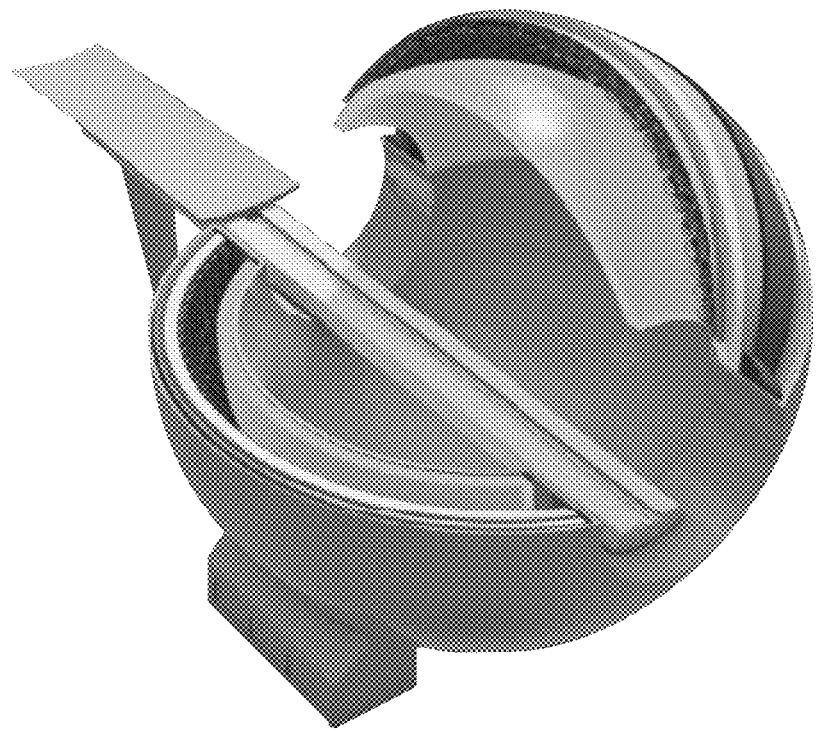

FIG. 19 and FIG. 20 illustrate example embodiments of an ABALONE PET scanner built either monolithically, or from a plurality of curving ABALONE radiation detector panels. In FIG. 19 an oblong scanner shape (e.g., cylinder with hemispherical end caps) is implemented, while in FIG. 20 a spherical shape is implemented. Both of these examples are shown with an entry hole and moving bed mounted for the introduction of the patient into the scanner cavity. In at least one embodiment, the entry hole can be covered by a sensor panel after patient entry into the device, so that gamma pairs can be registered in a fully surrounding surface of the ABALONE PET. Other embodiments can be provided in which the ABALONE PET opens (clamshell, door, hatch, etc.) for entry and positioning of the patient in any desired position, such as prone or standing, after which it is closed. It should be appreciated that an ABALONE PET may be implemented according to the present disclosure having a variety of curving exterior shapes (e.g., pill-shaped, barrel shaped, alternative ring design having a very small thickness in radial direction), without departing from the disclosed teachings In one embodiment, the ABALONE-PET is composed solely of the ABALONE radiation detector panels, which can be assembled into the structure of the unit at the point of application. They would preferably ship to the destination in the form of safely stacked panels in boxes, and a work crew would assemble them into a large structure of a desired shape and size. The design of the joining edges of the panels allows for a precise shape (various methods exist). Each radiation detector panel is connected to a central computer for processing the detection signals, such as utilizing a single cable, or any desired wired or wireless interfacing. This structure can be quickly disassembled, transported safely even in most unfavorable conditions (panels are resistant to water, sand, and strong vibration) to another place, and reassembled again.

The usefulness of the ABALONE-PET was discussed already in another section, particularly in comparison to prior art. The following summarizes the properties of this device: (a) large gamma-ray sensitive area that preferentially includes patient's body; (b) large internal diameter, satisfying ergonomic rules and still not too large as to significantly impact position resolution because of the non-colinearity effect, which in human tissue has an average standard deviation of 2 mrad; (c) low average incidence angle of gamma rays on the sensitive surfaces and a low parallax error, resulting in precise position resolution even with inexpensive scintillators (e.g., NaI(Tl)); (d) longer path for gamma rays between their creation points in human body and their detection points in the scintillators; (e) more relative accuracy in time-of-flight measurements for the gamma rays, than with devices having a smaller inner diameter; (f) the low parallax error confers an ability to utilize inexpensive scintillators (such as NaI(Tl)) of a high thickness and stopping power; (g) high intrinsic sensitivity to gamma rays, precise measurements of their energies and hit positions, in response to the superior performance of the ABALONE photon detectors; (h) reduced patient exposure to radioactivity during an examination; (i) transportability in the form of radiation detector panels, self-contained robust blocks which themselves present the building blocks of an ABALONE-PET; (j) transportability in harsh conditions (water, sand, ice, vibration), which is available in view of the robustness of the permanently sealed radiation detector panels.

Furthermore, another benefit is provided as the gamma rays, which undergo Compton scattering within the patient's body and thus slightly change their direction, will fly longer, and therefore their point of detection will form a line with the point of detection of the other gamma ray on the opposite side, that is shifted away more from the creation point than in smaller scanners. This deflection helps diffuse the noisy events (Compton scattered) away from the real sources, and reduce the confusion around the important real sources. For many Compton-scattered events the connection line, LOR, will even lie well outside patient's body, making their rejection trivial.

7. Conclusion

In conclusion, with its whole-body coverage, large internal diameter and advanced photon detectors, the ABALONE-PET scanner comes close to an ideal PET design within physical, ergonomic and financial constraints. It would provide detection of a maximum possible fraction of gamma-ray pairs emerging from patient's body with minimum parallax error, using the radiation dose administered to the patient in the most effective way (about 80 to 800 times lower than with prior art). The benefit-to-harm ratio would increase accordingly, resulting in wider population benefitting from early cancer detection screening, as well as other types of PET exams. ABALONE-PET is electronically and structurally robust, and can be easily assembled from its building blocks, and transported even in adverse environmental conditions.

From the description herein, it will be appreciated that that the present disclosure encompasses multiple embodiments which include, but are not limited to, the following:

1. A photo-radiation detector panel apparatus, comprising: (a) a base structure; (b) a plurality of photon detectors, each having a hemispherical window with a photocathode layer, and with an electron detector centered beneath the hemispherical window, each of said photon detectors having an electrical and physical connection to said base structure; and (c) an upper plate and a lower plate of said base structure between which is disposed an equipotential feedthrough chamber; (d) wherein said upper plate and said photocathode of each of said plurality of photon detectors is retained at a first voltage level, while said lower plate and a ring of material around said electron detector in said upper plate, are retained at a second voltage level, in which the difference between said first and second voltage level is a high voltage; (e) wherein photons striking said photocathode layer are converted to photoelectrons, which are then directed by electrostatic field lensing in response to local voltage gradients to said electron detector which outputs a signal; and (f) wherein said equipotential feedthrough chamber operates in combination with said photocathode layer of the hemispherical window and all other conductive surfaces to provide proper electrostatic lensing for the photoelectrons, by extending said electrical equipotential surfaces from said hemispherical window through said base structure between each of said plurality of photon detectors.

2. The apparatus of any preceding embodiment, wherein said electron detector comprises a scintillator layer positioned beneath said photocathode within said hemispherical window, and transmitting generated light to a photosensor mounted outside of said hemispherical window.

3. The apparatus of any preceding embodiment, wherein said photon detector comprises a scintillator based electron detector.

4. The apparatus of any preceding embodiment, wherein said scintillator in said scintillator based electron detector is selected from the group of scintillating materials consisting of YAP, YAG, GSO, LYSO, LSO, LaBr:Ce, and CeBr.

5. The apparatus of any preceding embodiment, wherein said equipotential feedthrough chamber extends equipotential surfaces within a base structure, instead of closing the equipotential surfaces in a dome structure behind each photon detector.

6. The apparatus of any preceding embodiment, wherein said upper plate comprises a printed circuit board (PCB).

7. The apparatus of any preceding embodiment, wherein said PCB comprises a material selected from the group of PCB material consisting of: copper-clad-fiberglass, G–10 board, glass, fused silica, quartz, Teflon, and Teflon composites.

8. The apparatus of any preceding embodiment, wherein said lower plate comprises a solid conductive material layer or a printed circuit board (PCB).

9. The apparatus of any preceding embodiment, wherein an electrical insulator is disposed between said upper plate and said lower plate as said equipotential feedthrough chamber.

10. The apparatus of any preceding embodiment, wherein power and signal line connections to said photon detector pass through a hollow conductive bridge connecting between said first and said second layers retained at said second voltage level.

11. The apparatus of any preceding embodiment, wherein said hemispherical window, photocathode, and said electron detector comprise a photon detector unit which is evacuated and hermetically sealed to maintain a vacuum in its evacuated space.

12. The apparatus of any preceding embodiment, further comprising a scintillator layer disposed over said hemispherical windows of said plurality of photon detectors, for providing conversion of gamma rays into visible light.

13. The apparatus of any preceding embodiment, further comprising a light distribution layer, disposed between said scintillator layer and said hemispherical windows of said plurality of photon detectors, for spreading photons generated in the scintillator over several of said photon detectors.

14. The apparatus of any preceding embodiment, further comprising a light distribution layer, disposed over said hemispherical windows of said plurality of photon detectors, for spreading photons generated in the scintillator over several of said photon detectors.

15. The apparatus of any preceding embodiment, wherein said position-sensitive photo-radiation detector panels are configured for use in detecting visible or UV light, or for detecting gamma-ray radiation.

16. The apparatus of any preceding embodiment, wherein said detector comprises a scintillator based gamma-ray detector; and wherein a sufficient number of said position-sensitive gamma-ray detector panels are interconnected into a substantially enclosed positron emission tomography (PET) system configured for detecting gamma-ray pairs.

17. The apparatus of any preceding embodiment, wherein said substantially enclosed PET system provides a detection envelope with three dimensional curving around both longitudinal axis, and transverse axis, of a patient's body, in which the three dimensional curving limits parallax error.

18. The apparatus of any preceding embodiment, wherein said substantially enclosed PET system is configured for imaging the entirety of the patient's body in a single scan without the need for sequential scanning operations while the body of a patient is moved through a PET scanner.

19. The apparatus of any preceding embodiment, wherein said substantially enclosed PET system has an inner diameter of 0.8 to 3 meters, and a length of from 2 to 4 meters.

20. A positron emission tomography (PET) apparatus, comprising: (a) a structure configured for substantially enclosing a patient during a PET scan; and (b) a plurality of gamma-ray detector panels retained within said structure, and configured for detecting gamma rays emerging from the patients entire body in a single PET scan.

21. A positron emission tomography (PET) apparatus, comprising: (a) a structure configured for substantially enclosing a patient during a PET scan; (b) a plurality of gamma-ray detector panels having a scintillator and a photon detector, said gamma-ray detector panels are retained within said structure, and configured for detecting gamma rays emerging from the patients entire body in a single PET scan; (c) a hemispherical window with a photocathode layer, and with a scintillator-based electron detector centered beneath the hemispherical window in each of said photon detectors, within which evacuated space is maintained; and (d) an upper plate and a lower plate having conductors for conveying a first and second voltage potential, between which is disposed an equipotential feedthrough chamber; (e) wherein said upper plate and said photocathode of each of said plurality of photon detectors is retained at a first voltage level, while said lower plate and a ring of material around said photo detector in said upper plate, are retained at a second voltage level, in which the difference between said first and second voltage level is a high voltage; (f) wherein photons striking said photocathode layer are converted to photoelectrons directed by electrical field lensing in response to local voltage gradients to said scintillator-based electron detector which outputs an amplified electronic signal; and (g) wherein said equipotential feedthrough chamber operates in combination with said photocathode layer of the hemispherical window to provide proper electrostatic lensing for the photoelectrons, by shaping said electrical equipotential surfaces for proper photoelectron focusing within the evacuated space below said hemispherical window, by extending said equipotential surfaces through said base structure between each of said plurality of photon detectors.

22. The apparatus of any preceding embodiment, wherein said PET apparatus provides a detection envelope with three dimensional curving around both longitudinal axis, and transverse axis, of a patient's body, in which the three dimensional curving limits parallax error.

23. The apparatus of any preceding embodiment, wherein said substantially enclosed PET apparatus captures gamma rays from all portions of the patient's body in a single scan without the need for sequential scanning operations during which the body of a patient must be moved through a PET scanner.

24. The apparatus of any preceding embodiment, wherein said PET apparatus has an inner diameter of 0.8 to 3 meters, and a length of from 2 to 4 meters.

25. The apparatus of any preceding embodiment, wherein said scintillator based electron detector utilizes a Geiger-mode Avalanche Photodiode (G-APD).

26. The apparatus of any preceding embodiment, wherein said scintillator in said scintillator based electron detector is selected from the group of scintillating materials, consisting of YAP, YAG, GSO, LYSO, LSO, LaBr:Ce, and CeBr.

27. The apparatus of any preceding embodiment, wherein said equipotential feedthrough chamber shapes the equipotential surfaces within the evacuated space between the hemispherical window and the base plate for proper photoelectron focusing from the photocathode layer to the electron detector, by extending those surfaces between said upper plate and lower plate.

28. The apparatus of any preceding embodiment, wherein said equipotential surfaces are extended between said upper plate and said lower plate instead of closing the equipotential surfaces in a rearward dome structure behind each photon detector.

29. The apparatus of any preceding embodiment, wherein said upper plate comprises a printed circuit board (PCB).

30. The apparatus of any preceding embodiment, wherein said PCB comprises a material selected from the group of PCB material consisting of: copper-clad-fiberglass, G-10 board, glass, fused silica, quartz, Teflon, and Teflon composites.

31. The apparatus of any preceding embodiment, wherein said lower plate comprises a solid conductive material layer or a printed circuit board (PCB).

32. The apparatus of any preceding embodiment, wherein an electrical insulator is disposed between said upper plate and said lower plate as said equipotential feedthrough chamber.

33. The apparatus of any preceding embodiment, wherein power and signal line connections to said photon detector pass through a hollow conductive bridge connecting between said first plate and said second plate retained at said second voltage level.

34. The apparatus of any preceding embodiment, wherein said hemispherical window with said electron sensor comprise a photon detector unit which is evacuated and hermetically sealed to maintain a vacuum in its evacuated space.

35. The apparatus of any preceding embodiment, further comprising a scintillator layer disposed over said hemispherical windows of said plurality of photon detectors, for providing conversion of gamma rays into visible light.

36. The apparatus of any preceding embodiment, further comprising a light distribution layer, disposed between said scintillator layer and said hemispherical windows of said plurality of photon detectors, for spreading photons generated in said scintillator over several of said photon detectors.

37. The apparatus of any preceding embodiment, further comprising a light distribution layer, disposed over said hemispherical windows of said plurality of photon detectors, for spreading photons generated in said scintillator over several of said photon detectors.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A photo-radiation detector panel apparatus, comprising:
(a) a base structure;
(b) a plurality of photon detectors in an array within said panel apparatus, each said photon detector having a hemispherical window with a photocathode layer, and with an electron detector centered beneath the hemispherical window, each of said photon detectors having an electrical and physical connection to said base structure; and
(c) an upper plate and a lower plate of said base structure between which is disposed an electrical insulator configured as an equipotential feedthrough chamber connecting hemispherical windows to adjacent photon detectors;
(d) wherein said upper plate comprises a broken conductive pattern in which there is no conductive material or resistive layer disposed between an inner conductive ring surrounding said electron detector and an outer conductive ring which is proximal said hemispherical window connecting to said photocathode of each hemispherical window of each said plurality of photon detectors which is retained at a first voltage level, while said lower plate and the inner conductive ring comprising a ring of material around said electron detector in said upper plate, are retained at a second voltage level, in which the difference between said first and second voltage level is a high voltage, with an electric field established between said first and said second voltage level;
(e) wherein the conductive pattern of said upper plate is broken with said electrical insulator exposed between the inner and outer conductive rings configured to extend the equipotential feedthrough channel for said electric field beneath the hemispherical windows to allow electrical equipotential lines under said hemispherical window to be carried as equipotential lines through said equipotential feedthrough chamber to underneath the hemispherical windows of adjacent photon detectors;
(f) wherein photons striking said photocathode layer are converted to photoelectrons, which are then directed by electrostatic field lensing in response to local voltage gradients to said electron detector which outputs a signal; and
(g) wherein said equipotential feedthrough chamber operates in combination with said photocathode layer of the hemispherical window and all other conductive surfaces to provide proper electrostatic lensing for the photoelectrons, by extending electrical equipotential surfaces from said hemispherical window through said base structure between each of said plurality of photon detectors.

2. The apparatus as recited in claim 1, wherein said electron detector comprises a scintillator layer positioned beneath said photocathode within said hemispherical window, and transmitting generated light to a photosensor mounted outside of said hemispherical window.

3. The apparatus as recited in claim 1, wherein said electron detector further comprises a scintillator layer of a scintillator.

4. The apparatus as recited in claim 3, wherein said scintillator layer of said scintillator of said electron detector is selected from the group of scintillating materials consisting of YAP, YAG, GSO, LYSO, LSO, LaBr:Ce, and CeBr.

5. The apparatus as recited in claim 1, wherein power and signal line connections to said photon detector pass through a hollow conductive bridge connecting between said upper plate and said lower plate of said base structure retained at said second voltage level.

6. The apparatus as recited in claim 1, wherein said hemispherical window, said photocathode, and said electron detector comprise a photon detector unit which is evacuated and hermetically sealed to maintain a vacuum in its evacuated space.

7. The apparatus as recited in claim 1, further comprising a scintillator layer disposed over said hemispherical windows of said plurality of photon detectors, for providing conversion of gamma rays into visible light.

8. The apparatus as recited in claim 7, further comprising a light distribution layer, disposed between said scintillator layer and said hemispherical windows of said plurality of photon detectors, for spreading photons generated in the scintillator over several of said photon detectors.

9. The apparatus as recited in claim 1, wherein said apparatus is configured for use in detecting visible or UV light, or for detecting gamma-ray radiation.

10. The apparatus as recited in claim 1, wherein said apparatus is configured as a scintillator based gamma-ray detector panel; and
wherein a sufficient number of said detector panels are interconnected into a substantially enclosed positron emission tomography (PET) system configured for detecting gamma-ray pairs.

11. The apparatus as recited in claim 10, wherein said substantially enclosed PET system provides a detection envelope with three dimensional curving around both longitudinal axis, and transverse axis, of a patient's body, in which the three dimensional curving limits parallax error.

12. The apparatus as recited in claim 10, wherein said substantially enclosed PET system is configured for imaging the entirety of the patient's body in a single scan without the need for sequential scanning operations while the body of a patient is moved through a PET scanner.

13. The apparatus as recited in claim 10, wherein said substantially enclosed PET system has an inner diameter of 0.8 to 3 meters, and a length of from 2 to 4 meters.

14. A positron emission tomography (PET) apparatus, comprising:
(a) a structure configured for substantially enclosing a patient during a PET scan;
(b) a plurality of gamma-ray detector panels having a scintillator and a photon detector, said gamma-ray detector panels are retained within said structure, and configured for detecting gamma rays emerging from the patient's entire body in a single PET scan;
(c) a hemispherical window with a photocathode layer, and with a scintillator-based electron detector centered beneath the hemispherical window in each of said photon detectors, within which evacuated space is maintained; and
(d) an upper plate and a lower plate of a base structure, having conductors for conveying a first and second voltage potential, between which is disposed an electrical insulator configured as an equipotential feedthrough chamber connecting hemispherical windows of adjacent photon detectors;
(e) wherein said upper plate comprises a broken conductive pattern in which there is no conductive material or resistive layer disposed between an inner conductive ring surrounding said electron detector and an outer conductive ring which is proximal said hemispherical window connecting to said photocathode of each hemispherical window of each of said plurality of photon detectors which is retained at a first voltage level, while said lower plate and the inner conductive ring comprising a ring of material around said scintillator-based electron detector in said upper plate, are retained at a second voltage level, in which the difference between said first and second voltage level is a high voltage, with an electric field established between said first and said second voltage level;
(f) wherein the conductive pattern of said upper plate is broken with said electrical insulator exposed between the inner and outer conductive rings configured to retain an equipotential feedthrough channel for said electric field beneath the hemispherical windows to allow electrical equipotential lines under said hemispherical window to be carried as equipotential lines through said equipotential feedthrough chamber to underneath the hemispherical windows of adjacent photon detectors;
(g) wherein photons striking said photocathode layer are converted to photoelectrons directed by electrical field lensing in response to local voltage gradients to said scintillator-based electron detector which outputs an amplified electronic signal; and
(h) wherein said equipotential feedthrough chamber operates in combination with said photocathode layer of the hemispherical window to provide proper electrostatic lensing for the photoelectrons, by shaping electrical equipotential surfaces for proper photoelectron focusing within the evacuated space below said hemispherical window, by extending said equipotential surfaces through said base structure between each of said plurality of photon detectors.

15. The apparatus as recited in claim 14, wherein said PET apparatus provides a detection envelope with three dimensional curving around both longitudinal axis, and transverse axis, of a patient's body, in which the three dimensional curving limits parallax error.

16. The apparatus as recited in claim 14, wherein said PET apparatus captures gamma rays from all portions of the patient's body in a single scan without the need for sequential scanning operations during which the body of a patient must be moved through a PET scanner.

17. The apparatus as recited in claim 14, wherein said PET apparatus has an inner diameter of 0.8 to 3 meters, and a length of from 2 to 4 meters.

18. The apparatus as recited in claim 14, wherein said scintillator based electron detector utilizes a Geiger-mode Avalanche Photodiode (G-APD).

19. The apparatus as recited in claim 14, wherein said scintillator in said scintillator based electron detector is selected from the group of scintillating materials, consisting of YAP, YAG, GSO, LYSO, LSO, LaBr:Ce, and CeBr.

20. The apparatus as recited in claim 14, wherein power and signal line connections to said photon detector pass through a hollow conductive bridge connecting between first plate and second plate retained at said second voltage level.

21. The apparatus as recited in claim 14, further comprising a scintillator layer within a second scintillator disposed over said hemispherical windows of said plurality of photon detectors, for providing conversion of gamma rays into visible light.

22. The apparatus as recited in claim 21, further comprising a light distribution layer, disposed between said scintillator layer within said scintillator and said hemispherical windows of said plurality of photon detectors, for spreading photons generated in said scintillator layer over several of said photon detectors.

23. The apparatus as recited in claim 14, further comprising a light distribution layer, disposed over said hemispherical windows of said plurality of photon detectors, for spreading photons generated in said scintillator over several of said photon detectors.

24. A photo-radiation detector panel apparatus, comprising:
   (a) a base structure;
   (b) a plurality of photon detectors in an array within said panel apparatus, each said photon detector having a hemispherical window with a photocathode layer, and with an electron detector centered beneath the hemispherical window, each of said photon detectors having an electrical and physical connection to said base structure; and
   (c) an upper plate and a lower plate of said base structure between which is disposed an electrical insulator configured as an equipotential feedthrough chamber connecting hemispherical windows to adjacent photon detectors;
   (d) wherein said upper plate comprises a conductive pattern disposed over said electrical insulator, wherein said conductive pattern has an inner conductive ring surrounding said electron detector, and an outer conductive ring proximal said hemispherical window, wherein said conductive pattern on said upper plate is broken with only exposed electrical insulator under each hemispherical window between said inner conductive ring and said outer conductive ring;
   (e) wherein said outer conductive ring is beneath, and is in electrical contact with, said photocathode layer of said hemispherical window and configured to retain said photocathode layer at a first voltage level;
   (f) wherein said inner conductive ring, which surrounds the electron detector, is configured for being retained at a second voltage level; and
   (g) wherein each said photon detector is configured to provide a high voltage difference between said first and said second voltage levels to establish an electric field;
   (h) wherein photons striking said photocathode layer are converted to photoelectrons, which are then directed by electrostatic field lensing in response to local voltage gradients to said electron detector which outputs a signal; and
   (i) wherein said equipotential feedthrough chamber operates in combination with said photocathode layer of the hemispherical window and all other conductive surfaces to provide proper electrostatic lensing for the photoelectrons, by extending electrical equipotential surfaces from said hemispherical window through said base structure between each of said plurality of photon detectors.

* * * * *